US009447403B2

(12) United States Patent
McNeely et al.

(10) Patent No.: US 9,447,403 B2
(45) Date of Patent: Sep. 20, 2016

(54) ENOLASE PEPTIDE CONJUGATE VACCINES AGAINST *STAPHYLOCOCCUS AUREUS*

(71) Applicant: Merck Sharp & Dohme Corp., Rahway, NJ (US)

(72) Inventors: Tessie B. McNeely, Gwynedd Valley, PA (US); Leslie Cope, Hatfield, PA (US); Sharon Smith, Downington, PA (US); Amita Joshi, Lansdale, PA (US); Irene Pak, New Brunswick, NJ (US); Arthur Fridman, East Norriton, PA (US)

(73) Assignee: Merck Sharp & Dohme Corp., Rahway, NJ (US)

( * ) Notice: Subject to any disclaimer, the term of this patent is extended or adjusted under 35 U.S.C. 154(b) by 73 days.

(21) Appl. No.: 14/045,433

(22) Filed: Oct. 3, 2013

(65) Prior Publication Data
US 2014/0030287 A1    Jan. 30, 2014

Related U.S. Application Data

(63) Continuation of application No. 13/884,828, filed as application No. PCT/US2011/060318 on Nov. 11, 2011, now abandoned.

(60) Provisional application No. 61/412,998, filed on Nov. 12, 2010.

(51) Int. Cl.
*C07K 14/31* (2006.01)
*A61K 39/085* (2006.01)
(Continued)

(52) U.S. Cl.
CPC .............. *C12N 9/88* (2013.01); *A61K 39/085* (2013.01); *C07K 14/31* (2013.01); *A61K 38/00* (2013.01); *A61K 2039/55505* (2013.01); *A61K 2039/6037* (2013.01)

(58) Field of Classification Search
CPC .............................. A61K 38/00; C07K 14/31
USPC .............................. 424/243.1, 234.1, 197.11
See application file for complete search history.

(56) References Cited

U.S. PATENT DOCUMENTS 6,521,441 B1 * 2/2003 Simpson et al. ........... 435/252.3
8,518,416 B2 * 8/2013 Pillich et al. .............. 424/243.1
(Continued)

FOREIGN PATENT DOCUMENTS

EP    0786519 A2    7/1997
EP    1987836 A1    11/2008
(Continued)

OTHER PUBLICATIONS

Molkanen, T et al, FEBS Letters, vol. 517, 2002, pp. 72-78, Enhanced activation of bound plasminogen on *Staphylococcus aureus* by staphylokinase.*
(Continued)

*Primary Examiner* — Albert Navarro
*Assistant Examiner* — Ginny Portner
(74) *Attorney, Agent, or Firm* — Henry P. Wu; Immac J. Thampoe

(57) ABSTRACT

The present invention relates to peptides of the enolase protein from *Staphylococcus aureus* as well as nucleic acid and nucleic acid sequence homologs encoding the peptides. The present invention also relates to a composition, particularly a *S. aureus* vaccine, comprising one or more of the enolase peptides described herein or a fragment, derivative or variant thereof capable of generating an immune response that induces a protective antibody response or opsonophagocytic activity of human neutrophils for *S. aureus*. The present invention also encompasses methods of treating and/or reducing the likelihood of a *Staphylococcus* infection by administering a composition of the invention.

3 Claims, 2 Drawing Sheets

```
  1 MPIITDVYAR EVLDSRGNPT VEVEVLTESG AFGRALVPSG ASTGEHEAVE LRDGDKSRYL
 61 GKGVTKAVEN VNEIIAPEII EGEFSVLDQV SIDKMMIALD GTPNKGKLGA NAILGVSIAV
121 ARAAADLLGQ PLYKYLGGFN GKQLPVPMMN IVNGGSHSDA PIAFQEFMIL PVGATTFKES
181 LRWGTEIFHN LKSILSKRGL ETAVGDEGGF APKFEGTEDA VETIIQAIEA AGYKPGEEVF
241 LGFDCASSEF YENGVYDYSK FEGEHGAKRT AAEQVDYLEQ LVDKYPIITI EDGMDENDWD
301 GWKQLTERIG DRVQLVGDDL FVTNTEILAK GIENGIGNSI LIKVNQIGTL TETFDAIEMA
361 QKAGYTAVVS HRSGETEDTT IADIAVATNA GQIKTGSLSR TDRIAKYNQL LRIEDELFET
421 AKYDGIKSFY NLDK (SEQ ID NO:8)
```

(51) Int. Cl.
C12N 9/88 (2006.01)
A61K 38/00 (2006.01)
A61K 39/00 (2006.01)

(56) References Cited

U.S. PATENT DOCUMENTS

| | | | |
|---|---|---|---|
| 2005/0053995 A1* | 3/2005 | Simpson et al. | 435/6 |
| 2006/0177462 A1 | 8/2006 | Anderson et al. | |
| 2008/0085289 A1 | 4/2008 | Castado et al. | |
| 2008/0299127 A1* | 12/2008 | Kroenke et al. | 424/139.1 |
| 2010/0003223 A1* | 1/2010 | Cifarelli et al. | 424/93.7 |
| 2015/0024469 A1* | 1/2015 | Briers et al. | 435/252.33 |

FOREIGN PATENT DOCUMENTS

| | | | |
|---|---|---|---|
| WO | WO01/98499 A1 | 12/2001 | |
| WO | WO02/059148 A2 | 8/2002 | |
| WO | 03/087352 * | 10/2003 | C12N 9/00 |
| WO | WO2005/009378 A2 | 2/2005 | |
| WO | WO2005/009379 A2 | 2/2005 | |
| WO | WO2005/79315 A2 | 9/2005 | |
| WO | WO2005/086663 A2 | 9/2005 | |
| WO | WO2005/115113 A2 | 12/2005 | |
| WO | WO2006/033918 A2 | 3/2006 | |
| WO | WO2006/078680 A2 | 7/2006 | |
| WO | WO2007/001361 A2 | 1/2007 | |
| WO | WO2010/062814 A1 | 6/2010 | |
| WO | WO2010/062815 A1 | 6/2010 | |
| WO | WO2012/009247 A1 | 1/2012 | |
| WO | WO2012/021229 A1 | 2/2012 | |

OTHER PUBLICATIONS

Bolotin, Alexander et al, Genome Research, vol. 11, pp. 731-753, 2001, The Complete Genome sequence of the Lactic Acid Bacterium *Lactococcus lactis* ssp. *lactis* IL 403.*

Rashel, M. et al, The Journal of Infectious Disease, 2007, vol. 196, pp. 1237-1247, Efficient Elimination of the Multidrug-Resistant *Staphylococcus aureus* by Cloned Lysin Derived from Bacteriophage oMR11.*

Li, Wen Qing, Immunisation with the glycolytic enzyme enolase confers effective protection against *Candida albicans* infection in mice, Vaccine, May 4, 2011, 5526-5533, vol. 29 No. 33.

Baba et al., 'Genome and virulence determinants of high virulence community-acquired MRSA' Lancet 359: 1819-1827 (2000).

Berzofsky et al., 'Strategies for designing and optimizing new generation vaccines'. 2001, Nature Reviews 1:209-219.

Brady et al., 'Identification of *Staphylococcus aureus* proteins recognized by the antibody-mediated immune response to a biofilm infection'. Infect. Immun., 74: 3415-26 (2006).

Clarke et al., 'Identification of in vivo-expressed antigens of *Staphylococcus aureus* and their use in vaccinations for protection against nasal carriage.' J. Infect. Dis. 193:1098-108 (2006).

Etz et al., 'Identification of in vivo expressed vaccine candidate antigens from *Staphylococcus aureus*' Proc. Natl. Acad. Sci. USA 99:6573-6578 (2002).

Gatlin et al., 'Proteomic profiling of cell envelope-associated proteins from *Staphylococcus aureus*.' Proteomics 6: 1530-49 (2006).

Glowalla et al., 'Proteomics-Based Identification of Anchorless Cell Wall Proteins as Vaccine Candidates against *Staphylococcus aureus*'. Infect. Immun., 77: 2719-2729 (2009).

Josefsson et al., 'Protection against Experimental *Staphylococcus aureus* Arthritis by Vaccination with Clumping Factor A, a Novel Virulence Determinant' J. Infect. Dis. 184: 1572-1580 (2001).

Joyce et al., 'Isolation, structural characterization, and immunological evaluation of a high-molecular-weight exopolysaccharide from *Staphylococcus aureus*' Carbohydrate Research 338:903-922 (2003).

Kuroda et al., 'Whole genome sequencing of meticillin-resistant *Staphylococcus aureus*' Lancet 357: 1225-1240 (2001).

Lowy et al., '*Staphylococcus aureus* infections.' N. Engl. J. Med. 339:520-32 (1998).

Mamo et al., "Vaccination with *Staphylococcus aureus* fibrinogen binding proteins (FgBPs) reduces colonisation of *S. aureus* in a mouse mastitis model" FEMS Immunol. Med. Mic. 10:47-54 (1994).

Nandakumar et al., 'Proteome analysis of membrane and cell wall associated proteins from *Staphylococcus aureus*.' J. Proteome Res., 4: 250-7(2005).

Nilsson et al., 'Vaccination with a Recombinant Fragment of Collagen Adhesin Provides Protection against *Staphylococcus aureus*-mediated Septic Death' J. Clin. Invest. 101: 2640-2649 (1998).

Palazzo et al., 'First report of vancomycin-resistant *Staphylococci* isolated from healthy carriers in Brazil.' J. Clin. Microbiol. 43: 179-85 (2005).

Pieper et al., 'Comparative proteomic analysis of *Staphylococcus aureus* strains with differences in resistance to the cell wall-targeting antibiotic vancomycin.' Proteomics 6: 4246-58 (2006).

Selvey et al., 'Nosocomial methicillin-resistant *Staphylococcus aureus* bacteremia: is it any worse than nosocomial methicillin-sensitive *Staphylococcus aureus* bacteremia?' Infect. Control. Hosp. Epidemiol. 21: 645-8 (2000).

Shinefield et al., 'Use of a *Staphylococcus aureus* conjugate vaccine in patients receiving hemodialysis' N. Eng. J. Med. 346: 491-496 (2002).

Stranger-Jones et al., 'Vaccine assembly from surface proteins of *Staphylococcus aureus*.' Proc. Natl. Acad. Sci., USA 103:16942-7 (2006).

Tenover et al., 'Increasing resistance to vancomycin and other glycopeptides in *Staphylococcus aureus*.' Emerg. Infect. Dis. 7: 327-32 (2001).

Tenover et al., 'Characterization of *Staphylococci* with reduced susceptibilities to vancomycin and other glycopeptides.' J. Clin. Microbiol. 36: 1020-7 (1998).

Vytvytska et al., 'Identification of vaccine candidate antigens of *Staphylococcus aureus* by serological proteome analysis.' Proteomics 2: 580-90 (2002).

Weichhart et al., 'Functional selection of vaccine candidate peptides from *Staphylococcus aureus* whole-genome expression libraries in vitro.' Infect. Immun. 71: 4633-41 (2003).

Yang et al., 'A novel peptide isolated from phage library to substitute a complex system for a vaccine against *Staphylococci* infection.' Vaccine 24: 1117-23 (2006).

* cited by examiner

```
  1 MPIITDVYAR EVLDSRGNPT VEVEVLTESG AFGRALVPSG ASTGEHEAVE LRDGDKSRYL
 61 GKGVTKAVEN VNEIIAPEII EGEFSVLDQV SIDKMMIALD GTPNKGKLGA NAILGVSIAV
121 ARAAADLLGQ PLYKYLGGFN GKQLPVPMMN IVNGGSHSDA PIAFQEFMIL PVGATTFKES
181 LRWGTEIFHN LKSILSKRGL ETAVGDEGGF APKFEGTEDA VETIIQAIEA AGYKPGEEVF
241 LGFDCASSEF YENGVYDYSK FEGEHGAKRT AAEQVDYLEQ LVDKYPIITI EDGMDENDWD
301 GWKQLTERIG DRVQLVGDDL FVTNTEILAK GIENGIGNSI LIKVNQIGTL TETFDAIEMA
361 QKAGYTAVVS HRSGETEDTT IADIAVATNA GQIKTGSLSR TDRIAKYNQL LRIEDELFET
421 AKYDGIKSFY NLDK (SEQ ID NO:8)
```

FIG. 1

SEQUENCE LISTING

```
<160> NUMBER OF SEQ ID NOS: 12

<210> SEQ ID NO 1
<211> LENGTH: 18
<212> TYPE: PRT
<213> ORGANISM: Artificial Sequence
<220> FEATURE:
<223> OTHER INFORMATION: Enolase 213-230 peptide from S. aureus COL

<400> SEQUENCE: 1

Lys Phe Glu Gly Thr Glu Asp Ala Val Glu Thr Ile Ile Gln Ala Ile
1               5                   10                  15

Glu Ala

<210> SEQ ID NO 2
<211> LENGTH: 16
<212> TYPE: PRT
<213> ORGANISM: Artificial Sequence
<220> FEATURE:
<223> OTHER INFORMATION: Enolase 419-434 peptide from S. aureus COL

<400> SEQUENCE: 2

Glu Thr Ala Lys Tyr Asp Gly Ile Lys Ser Phe Tyr Asn Leu Asp Lys
1               5                   10                  15

<210> SEQ ID NO 3
<211> LENGTH: 33
<212> TYPE: PRT
<213> ORGANISM: Artificial Sequence
<220> FEATURE:
<223> OTHER INFORMATION: His-tagged Enolase 213-230 peptide

<400> SEQUENCE: 3

Met Gly His His His His His His His His Lys Phe Glu Gly
1               5                   10                  15

Thr Glu Asp Ala Val Glu Thr Ile Ile Gln Ala Ile Glu Ala Ala Glu
            20                  25                  30

Gln

<210> SEQ ID NO 4
<211> LENGTH: 31
<212> TYPE: PRT
<213> ORGANISM: Artificial Sequence
<220> FEATURE:
<223> OTHER INFORMATION: His-tagged Enolase 419-434 peptide

<400> SEQUENCE: 4

Met Gly His His His His His His His His Glu Thr Ala Lys
1               5                   10                  15

Tyr Asp Gly Ile Lys Ser Phe Tyr Asn Leu Asp Lys Ala Glu Gln
            20                  25                  30
```

```
<210> SEQ ID NO 5
<211> LENGTH: 13
<212> TYPE: PRT
<213> ORGANISM: Artificial Sequence
<220> FEATURE:
<223> OTHER INFORMATION: Enolase 325-337 peptide from S. aureus COL

<400> SEQUENCE: 5

Thr Glu Ile Leu Ala Lys Gly Ile Glu Asn Gly Ile Gly
1               5                   10

<210> SEQ ID NO 6
<211> LENGTH: 33
<212> TYPE: PRT
<213> ORGANISM: Artificial Sequence
<220> FEATURE:
<223> OTHER INFORMATION: Enolase 252-284 peptide from S. aureus COL

<400> SEQUENCE: 6

Glu Asn Gly Val Tyr Asp Tyr Ser Lys Phe Glu Gly Glu His Gly Ala
1               5                   10                  15

Lys Arg Thr Ala Ala Glu Gln Val Asp Tyr Leu Glu Gln Leu Val Asp
            20                  25                  30

Lys

<210> SEQ ID NO 7
<211> LENGTH: 645
<212> TYPE: PRT
<213> ORGANISM: S. aureus

<400> SEQUENCE: 7

Met Asn Lys Gln Gln Lys Glu Phe Lys Ser Phe Tyr Ser Ile Arg Lys
1               5                   10                  15

Ser Ser Leu Gly Val Ala Ser Val Ala Ile Ser Thr Leu Leu Leu Leu
            20                  25                  30

Met Ser Asn Gly Glu Ala Gln Ala Ala Glu Glu Thr Gly Gly Thr
            35                  40                  45

Asn Thr Glu Ala Gln Pro Lys Thr Glu Ala Val Ala Ser Pro Thr Thr
    50                  55                  60

Thr Ser Glu Lys Ala Pro Glu Thr Lys Pro Val Ala Asn Ala Val Ser
65                  70                  75                  80

Val Ser Asn Lys Glu Val Glu Ala Pro Thr Ser Glu Thr Lys Glu Ala
                85                  90                  95

Lys Glu Val Lys Glu Val Lys Ala Pro Lys Glu Thr Lys Glu Val Lys
            100                 105                 110

Pro Ala Ala Lys Ala Thr Asn Asn Thr Tyr Pro Ile Leu Asn Gln Glu
        115                 120                 125

Leu Arg Glu Ala Ile Lys Asn Pro Ala Ile Lys Asp Lys Asp His Ser
    130                 135                 140

Ala Pro Asn Ser Arg Pro Ile Asp Phe Glu Met Lys Lys Lys Asp Gly
145                 150                 155                 160

Thr Gln Gln Phe Tyr His Tyr Ala Ser Ser Val Lys Pro Ala Arg Val
                165                 170                 175

Ile Phe Thr Asp Ser Lys Pro Glu Ile Glu Leu Gly Leu Gln Ser Gly
            180                 185                 190

Gln Phe Trp Arg Lys Phe Glu Val Tyr Glu Gly Asp Lys Lys Leu Pro
        195                 200                 205

Ile Lys Leu Val Ser Tyr Asp Thr Val Lys Asp Tyr Ala Tyr Ile Arg
    210                 215                 220
```

```
Phe Ser Val Ser Asn Gly Thr Lys Ala Val Lys Ile Val Ser Ser Thr
225                 230                 235                 240

His Phe Asn Asn Lys Glu Glu Lys Tyr Asp Tyr Thr Leu Met Glu Phe
                245                 250                 255

Ala Gln Pro Ile Tyr Asn Ser Ala Asp Lys Phe Lys Thr Glu Glu Asp
            260                 265                 270

Tyr Lys Ala Glu Lys Leu Leu Ala Pro Tyr Lys Lys Ala Lys Thr Leu
        275                 280                 285

Glu Arg Gln Val Tyr Glu Leu Asn Lys Ile Gln Asp Lys Leu Pro Glu
    290                 295                 300

Lys Leu Lys Ala Glu Tyr Lys Lys Lys Leu Glu Asp Thr Lys Lys Ala
305                 310                 315                 320

Leu Asp Glu Gln Val Lys Ser Ala Ile Thr Glu Phe Gln Asn Val Gln
                325                 330                 335

Pro Thr Asn Glu Lys Met Thr Asp Leu Gln Asp Thr Lys Tyr Val Val
            340                 345                 350

Tyr Glu Ser Val Glu Asn Asn Glu Ser Met Met Asp Thr Phe Val Lys
        355                 360                 365

His Pro Ile Lys Thr Gly Met Leu Asn Gly Lys Lys Tyr Met Val Met
370                 375                 380

Glu Thr Thr Asn Asp Asp Tyr Trp Lys Asp Phe Met Val Glu Gly Gln
385                 390                 395                 400

Arg Val Arg Thr Ile Ser Lys Asp Ala Lys Asn Asn Thr Arg Thr Ile
                405                 410                 415

Ile Phe Pro Tyr Val Glu Gly Lys Thr Leu Tyr Asp Ala Ile Val Lys
            420                 425                 430

Val His Val Lys Thr Ile Asp Tyr Asp Gly Gln Tyr His Val Arg Ile
        435                 440                 445

Val Asp Lys Glu Ala Phe Thr Lys Ala Asn Thr Asp Lys Ser Asn Lys
450                 455                 460

Lys Glu Gln Gln Asp Asn Ser Ala Lys Lys Glu Ala Thr Pro Ala Thr
465                 470                 475                 480

Pro Ser Lys Pro Thr Pro Ser Pro Val Glu Lys Glu Ser Gln Lys Gln
                485                 490                 495

Asp Ser Gln Lys Asp Asp Asn Lys Gln Leu Pro Ser Val Glu Lys Glu
            500                 505                 510

Asn Asp Ala Ser Ser Glu Ser Gly Lys Asp Lys Thr Pro Ala Thr Lys
        515                 520                 525

Pro Thr Lys Gly Glu Val Glu Ser Ser Thr Thr Pro Thr Lys Val
530                 535                 540

Val Ser Thr Thr Gln Asn Val Ala Lys Pro Thr Thr Ala Ser Ser Lys
545                 550                 555                 560

Thr Thr Lys Asp Val Val Gln Thr Ser Ala Gly Ser Ser Glu Ala Lys
                565                 570                 575

Asp Ser Ala Pro Leu Gln Lys Ala Asn Ile Lys Asn Thr Asn Asp Gly
            580                 585                 590

His Thr Gln Ser Gln Asn Asn Lys Asn Thr Gln Glu Asn Lys Ala Lys
        595                 600                 605

Ser Leu Pro Gln Thr Gly Glu Glu Ser Asn Lys Asp Met Thr Leu Pro
    610                 615                 620

Leu Met Ala Leu Leu Ala Leu Ser Ser Ile Val Ala Phe Val Leu Pro
625                 630                 635                 640
```

Arg Lys Arg Lys Asn
            645

<210> SEQ ID NO 8
<211> LENGTH: 434
<212> TYPE: PRT
<213> ORGANISM: S. aureus

<400> SEQUENCE: 8

Met Pro Ile Ile Thr Asp Val Tyr Ala Arg Glu Val Leu Asp Ser Arg
1               5                   10                  15

Gly Asn Pro Thr Val Glu Val Glu Val Leu Thr Glu Ser Gly Ala Phe
            20                  25                  30

Gly Arg Ala Leu Val Pro Ser Gly Ala Ser Thr Gly Glu His Glu Ala
        35                  40                  45

Val Glu Leu Arg Asp Gly Asp Lys Ser Arg Tyr Leu Gly Lys Gly Val
    50                  55                  60

Thr Lys Ala Val Glu Asn Val Asn Glu Ile Ile Ala Pro Glu Ile Ile
65                  70                  75                  80

Glu Gly Glu Phe Ser Val Leu Asp Gln Val Ser Ile Asp Lys Met Met
                85                  90                  95

Ile Ala Leu Asp Gly Thr Pro Asn Lys Gly Lys Leu Gly Ala Asn Ala
            100                 105                 110

Ile Leu Gly Val Ser Ile Ala Val Ala Arg Ala Ala Ala Asp Leu Leu
        115                 120                 125

Gly Gln Pro Leu Tyr Lys Tyr Leu Gly Gly Phe Asn Gly Lys Gln Leu
    130                 135                 140

Pro Val Pro Met Met Asn Ile Val Asn Gly Gly Ser His Ser Asp Ala
145                 150                 155                 160

Pro Ile Ala Phe Gln Glu Phe Met Ile Leu Pro Val Gly Ala Thr Thr
                165                 170                 175

Phe Lys Glu Ser Leu Arg Trp Gly Thr Glu Ile Phe His Asn Leu Lys
            180                 185                 190

Ser Ile Leu Ser Lys Arg Gly Leu Glu Thr Ala Val Gly Asp Glu Gly
        195                 200                 205

Gly Phe Ala Pro Lys Phe Glu Gly Thr Glu Asp Ala Val Glu Thr Ile
    210                 215                 220

Ile Gln Ala Ile Glu Ala Ala Gly Tyr Lys Pro Gly Glu Glu Val Phe
225                 230                 235                 240

Leu Gly Phe Asp Cys Ala Ser Ser Glu Phe Tyr Glu Asn Gly Val Tyr
                245                 250                 255

Asp Tyr Ser Lys Phe Glu Gly Glu His Gly Ala Lys Arg Thr Ala Ala
            260                 265                 270

Glu Gln Val Asp Tyr Leu Glu Gln Leu Val Asp Lys Tyr Pro Ile Ile
        275                 280                 285

Thr Ile Glu Asp Gly Met Asp Glu Asn Asp Trp Asp Gly Trp Lys Gln
    290                 295                 300

Leu Thr Glu Arg Ile Gly Asp Arg Val Gln Leu Val Gly Asp Asp Leu
305                 310                 315                 320

Phe Val Thr Asn Thr Glu Ile Leu Ala Lys Gly Ile Glu Asn Gly Ile
                325                 330                 335

Gly Asn Ser Ile Leu Ile Lys Val Asn Gln Ile Gly Thr Leu Thr Glu
            340                 345                 350

Thr Phe Asp Ala Ile Glu Met Ala Gln Lys Ala Gly Tyr Thr Ala Val
        355                 360                 365

```
Val Ser His Arg Ser Gly Glu Thr Glu Asp Thr Thr Ile Ala Asp Ile
    370                 375                 380

Ala Val Ala Thr Asn Ala Gly Gln Ile Lys Thr Gly Ser Leu Ser Arg
385                 390                 395                 400

Thr Asp Arg Ile Ala Lys Tyr Asn Gln Leu Leu Arg Ile Glu Asp Glu
                405                 410                 415

Leu Phe Glu Thr Ala Lys Tyr Asp Gly Ile Lys Ser Phe Tyr Asn Leu
                420                 425                 430

Asp Lys

<210> SEQ ID NO 9
<211> LENGTH: 57
<212> TYPE: DNA
<213> ORGANISM: Artificial Sequence
<220> FEATURE:
<223> OTHER INFORMATION: Nucleotide sequence encoding Enolase 213-230
      peptide from S. aureus COL

<400> SEQUENCE: 9
aaatttgaag gtactgaaga tgctgttgaa acaattatcc aagcaatcga agcagct          57

<210> SEQ ID NO 10
<211> LENGTH: 48
<212> TYPE: DNA
<213> ORGANISM: Artificial Sequence
<220> FEATURE:
<223> OTHER INFORMATION: Nucleotide sequence encoding Enolase 419-434
      peptide from S. aureus COL

<400> SEQUENCE: 10
gaaactgcta aatatgacgg tatcaaatca ttctataact tagataaa                    48

<210> SEQ ID NO 11
<211> LENGTH: 39
<212> TYPE: DNA
<213> ORGANISM: Artificial Sequence
<220> FEATURE:
<223> OTHER INFORMATION: Nucleotide sequence encoding Enolase 325-337
      peptide from S. aureus COL

<400> SEQUENCE: 11
actgaaattt tagcaaaagg tattgaaaac ggaattggt                              39

<210> SEQ ID NO 12
<211> LENGTH: 99
<212> TYPE: DNA
<213> ORGANISM: Artificial Sequence
<220> FEATURE:
<223> OTHER INFORMATION: Nucleotide sequence encoding Enolase 252-284
      peptide from S. aureus COL

<400> SEQUENCE: 12
gaaaatggtg tatatgacta cagtaagttc gaaggcgaac acggtgcaaa acgtacagct       60
gcagaacaag ttgactactt agaacaatta gtagacaaa                              99
```

ENOLASE PEPTIDE CONJUGATE VACCINES AGAINST *STAPHYLOCOCCUS AUREUS*

CROSS-REFERENCE TO RELATED APPLICATIONS

This application is a continuation of U.S. application Ser. No. 13/884,828, which is a §371 National Stage Application of PCT/US2011/060318, international filing date of Nov. 11, 2011, which claims the benefit of U.S. Provisional Application No. 61/412,998, filed Nov. 12, 2010, the contents of which are hereby incorporated by reference in their entirety.

REFERENCE TO SEQUENCE LISTING SUBMITTED ELECTRONICALLY

The sequence listing of the present application is submitted electronically via EFS-Web as an ASCII formatted sequence listing with a file name "MRLIFD00028USCNT-SEQLIST-03OCT2013.TXT", creation date of Oct. 3, 2013, and a size of 12.6 KB. This sequence listing submitted via EFS-Web is part of the specification and is herein incorporated by reference in its entirety.

FIELD OF THE INVENTION

The present invention relates to peptides of the enolase protein from *Staphylococcus aureus* as well as nucleic acid sequence encoding said peptides. The present invention also relates to compositions, particularly *S. aureus* vaccines, comprising one or more peptides of the enolase protein with a pharmaceutically acceptable carrier, wherein the peptides are capable of generating an immune response that induces responses such as protective antibody formation and opsonophagocytic activity of human neutrophils for *S. aureus*, as well as methods of use of the compositions.

BACKGROUND OF THE INVENTION

*Staphylococcus aureus* is a nosocomial as well as a community-acquired pathogen, which causes a wide range of diseases and conditions, from minor skin infections to serious life-threatening conditions such as bacteraemia, endocarditis, pneumonia, toxic shock syndrome and wound infections. See Lowy et al., *N Engl. J. Med.* 339:520-32 (1998). Other examples of diseases and conditions caused by *S. aureus* include botryomyosis, bullous impetigo, carbuncle, cellulitis, central nervous system infections, folliculitis, furuncle, impetigo, infective and inflammatory eye disease, osteomyelitis and other infections of joints and bones, respiratory tract infections, and scalded skin syndrome. See *The Staphylococci in Human Disease*, Crossley and Archer (eds.), Churchill Livingstone Inc., 1997.

The worldwide growing incidence of staphylococcal infections is strongly related to the increased use of surgical devices and a growing number of immunocompromised patients. The situation has become more serious since the increased use of antibiotics has led to the emergence of methicillin-resistant *S. aureus* strains (MRSA). See Selvey et al., *Infect. Control. Hosp. Epidemiol.* 21: 645-8 (2000); Peacock et al., *Ann. Intern. Med.* 93: 526-32 (1980). More recently, *S. aureus* isolates with reduced susceptibility to vancomycin, the antibiotic of choice against MRSA strains, and isolates with vancomycin-resistance have been described. See Tenover et al., *Emerg. Infect. Dis.* 7: 327-32 (2001); Tenover et al., *J. Clin. Microbiol.* 36: 1020-7 (1998); and Palazzo et al., *J. Clin. Microbiol.* 43: 179-85 (2005). The rising emergence of multidrug-resistant staphylococci has led to a growing interest in the development of alternative approaches to prevent and treat *staphylococcal* infections.

A vaccine targeting *S. aureus* can be achieved using suitable *S. aureus* polysaccharides or peptides as vaccine components. Examples of polysaccharides that may be employed as possible vaccine components include *S. aureus* type 5 and type 8 capsular polysaccharides. See Shinefield et al., *N. Eng. J. Med.* 346: 491-496 (2002). Examples of peptides that may be employed as possible vaccine components include clumping factor, collagen adhesin, and fibrinogen binding proteins. See Mamo et al., *FEMS Immunol. Med. Mic.* 10: 47-54 (1994); Nilsson et al., *J. Clin. Invest.* 101: 2640-2649 (1998); Josefsson et al., *J. Infect. Dis.* 184: 1572-1580 (2001). A multivalent vaccine consisting of four antigenic determinants has been shown to provide protection against lethal challenge with *S. aureus*. See Stranger-Jones et al., *Proc. Natl. Acad. Sci., USA* 103:16942-7 (2006).

Information concerning *S. aureus* peptide sequences has been obtained from sequencing the *S. aureus* genome. See Kuroda et al., Lancet 357: 1225-1240 (2001); Baba et al., Lancet 359: 1819-1827 (2000); European Patent Publication EP 0 786 519. To some extent, bioinformatics has been employed in efforts to characterize peptide sequences obtained from genome sequencing. See, e.g., European Patent Publication EP 0 786 519.

Techniques such as those involving display technology and sera from infected patients have also been used in an effort to help identify genes coding for potential antigens. See, e.g., International Publication Nos. WO 01/98499 and WO 02/059148; and Etz et al., *Proc. Natl. Acad. Sci. USA* 99:6573-6578 (2002).

Staphylococcal surface proteins have been identified using recently adopted technologies, like proteomics (see Brady et al., *Infect. Immun.*, 74: 3415-26 (2006); Gatlin et al., *Proteomics* 6: 1530-49 (2006); Pieper et al., *Proteomics* 6: 4246-58 (2006); Vytvytska et al., *Proteomics* 2: 580-90 (2002); Nandakumar et al., *J. Proteome Res.*, 4: 250-7 (2005)) or protein selection methods based on expression libraries (see Clarke et al., *J. Infect. Dis.* 193:1098-108 (2006); Etz et al., *Proc. Natl. Acad. Sci. USA* 99: 6573-8 (2002); Weichhart et al., *Infect. Immun.* 71: 4633-41 (2003); and Yang et al., *Vaccine* 24: 1117-23 (2006)). Unfortunately, the usefulness of most antigens as vaccine candidates is not supported by studies demonstrating functional activity in vivo. Dozens of *S. aureus* antigens have been tested in accepted animal model systems, but most have failed to provide protective immunity following challenge with *S. aureus*. Despite the reported ability of some immunogens to provide protection in animal models, there are no reported protein-based vaccines for *staphylococcal* infections in humans or animals to date. Thus, there remains a need for immunogenic compositions that can provide protective immunity against *Staphylococcal* infections in human and/or animals.

Citation or identification of any reference in this section or any other section of this application shall not be construed as an indication that such reference is available as prior art to the present invention.

SUMMARY OF THE INVENTION

The present invention relates to peptides of the enolase protein, which is present in all tested strains of *S. aureus*. The enolase protein from *S. aureus* has been investigated as a candidate vaccine antigen. When used as an antigen, the full length enolase protein failed to induce a protective immune response in mice. (Glowalla et al., *Infect. and Imm.*, 77: 2719-2729 (2009)). However, it is shown herein that enolase peptides can provide protective immunity against *S. aureus* infection.

Accordingly, the present invention provides an isolated peptide according to SEQ ID NOs: 1, 2, 5 or 6 or fragments, variants or derivatives thereof, and uses of such peptides. For example, it is shown herein that a derivative of the peptides containing an amino His-tag and additional carboxyl amino acids can produce a protective immune response against *S. aureus*.

A first aspect of the invention provides a peptide having the amino acid sequence of SEQ ID NO: 1, 2, 5 or 6, or fragments, variants or derivatives thereof. In one embodiment, the peptide consists of the amino acid sequence of SEQ ID NO: 1, 2, 5 or 6 or is a derivative thereof. In another embodiment, a derivative of the peptides includes one or more additional regions or moieties covalently joined to the peptide, wherein each region or moiety is independently selected from a region or moiety having at least one of the following properties: enhances the immune response, facilitates purification, or facilitates peptide stability. In certain embodiments, the additional regions or moieties are covalently joined at the carboxyl terminus or amino terminus Additional region or moiety indicates a region or moiety different from a *S. aureus* enolase peptide. The additional region or moiety can be, for example, an additional peptide region or a non-peptide region. In one embodiment, a derivative consists of the amino acid sequence of SEQ ID NO: 1, 2, 5 or 6 together with an N-terminal methionine. In certain embodiments, the peptide comprises, or alternatively, consists of, the peptide of SEQ ID NO: 1, 2, 5 or 6. The peptide may be substantially purified. In certain embodiments, the peptide provides protective immunity against *S. aureus*.

A second aspect of the invention provides a composition able to induce protective immunity against *S. aureus* in a patient comprising an immunologically effective amount of one or more enolase peptides or a fragment, variant or derivative thereof, and a pharmaceutically acceptable carrier. Preferably, said composition is a pharmaceutical and/or immunogenic composition such as a vaccine. An immunologically effective amount is an amount sufficient to provide protective immunity against *S. aureus* infection. The amount should be sufficient to significantly prevent the likelihood or severity of a *S. aureus* infection. In other embodiments, the composition comprises or more of the peptides described above. In certain embodiments, the composition further comprises an adjuvant.

A third aspect of the invention provides methods of treating and/or preventing *S. aureus* infection in a patient comprising administrating a immunologically effective amount of a composition of the invention to said patient. Said methods induce a protective immune response against *S. aureus* infection in a patient. In one embodiment, the patient is a human. In certain embodiments, the human is immunocompromised. An immunocompromised patient can be an elderly patient, an infant or young child, or a patient with a disease such as AIDS. In alternative embodiments, the patient is an animal.

A fourth aspect of the invention provides a use of an immunologically effective amount of a peptide according to SEQ ID NO: 1, 2, 5 or 6, or a fragment, variant or derivative thereof, in the manufacture of a medicament for inducing a protective immune response in a patient against *S. aureus* infection.

A fifth aspect of the invention provides an isolated nucleic acid sequence encoding an enolase peptide or fragment, variant or derivative thereof, such as an enolase peptide having or consisting a sequence of amino acids as set forth in SEQ ID NO: 1, 2, 5, or 6. In one embodiment, the sequence comprises or consists of the nucleotide sequence set forth in SEQ ID NO: 9, 10, 11, or 12.

A sixth aspect of the invention provides an expression vector comprising a nucleic acid sequence in the fifth aspect wherein said sequence is operably linked to transcriptional and translational regulatory nucleic acid.

A seventh aspect of the invention provides a host cell containing an expression vector of the invention.

An eight aspect of the invention provides a method of producing a recombinant enolase peptide, or a fragment, variant or derivative thereof, said method comprising the steps of:

(a) culturing a host cell containing an expression vector comprising a DNA sequence encoding SEQ ID NO: 1, 2, 5 or 6, or a portion thereof, such that said recombinant peptide is expressed from said nucleic acid; and (b) isolating said recombinant peptide. In other embodiments, the method produces any of the peptides described above.

BRIEF DESCRIPTION OF THE DRAWINGS

FIG. 1 shows the full-length amino acid sequence of the enolase protein from *S. aureus* strain COL (SEQ ID NO 8). Also shown (bold, underlined sequences) are the locations of *S. aureus* enolase peptides of the invention as represented by SEQ ID NOs: 1, 2, 5 and 6.

DETAILED DESCRIPTION OF THE INVENTION

Figure 2:
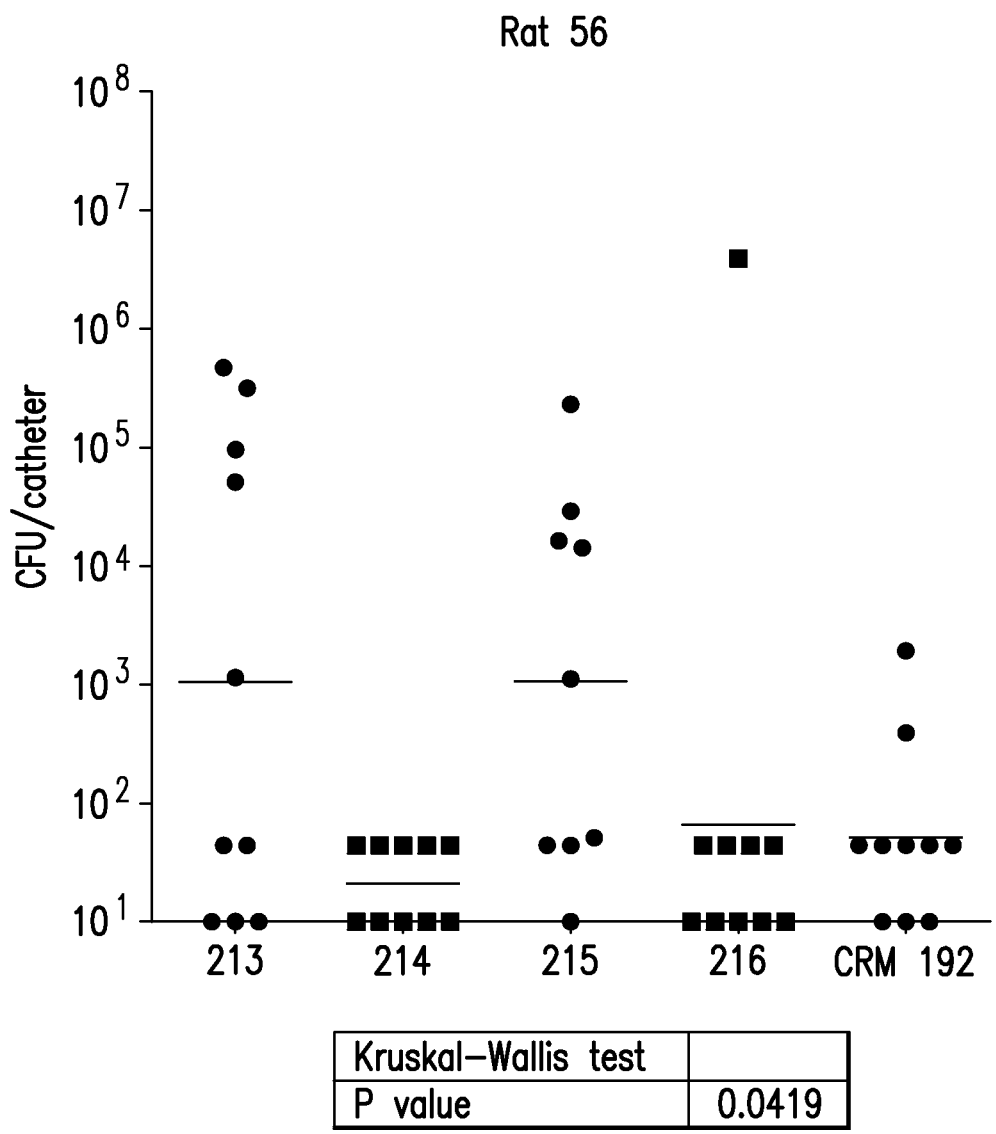
FIG. 2 shows results of an immunogenicity study using a rat indwelling catheter model, as described in Example 4. Shown are the numbers of CFU/catheter for rats that were immunized with enolase peptides 213-216 conjugated to CRM 192 or CRM 192 alone and challenged with *S. aureus* strain Becker.

The present invention is based at least in part, on the identification of peptides of enolase, a conserved surface protein, using a computational mathematics approach. Enolase is expressed during times when the critical nutrient, iron, is available in extremely limited quantity. This situation is reflective of the internal human environment. Therefore, enolase is expressed during infection of the human body, and allows stimulation of the immune system, for clearance of bacteria. Enolase may also be expressed in other environments, such as in biofilm growth conditions.

FIG. 1 provides the full-length peptide sequence of the *S. aureus* enolase protein from the COL strain (SA0482, SEQ ID NO:8) and shows the location of representative peptides of the invention (SEQ ID NO:1, 2, 5 and 6). Full-length enolase protein has been demonstrated to be an ineffective vaccine candidate due to its inability to provide protective immunity against *S. aureus* infection (Glowalla et al., supra). However, a derivative of SEQ ID NO: 1, 2, 5 or 6 containing an NH$_2$-terminal histidine-tag ("his-tag") and three additional carboxyl amino acids was found to produce a protective immune response against *S. aureus*. The his-tag was added to facilitate peptide purification.

Accordingly, the present invention provides an isolated peptide according to SEQ ID NOs: 1, 2, 5 or 6, or a fragment, variant, or derivative thereof. In an embodiment, the peptides, fragments, variants and derivatives of the invention elicit a protective immune response against a *S. aureus* strain, such as, but not limited to the following strains: COL, Becker, MW2, N315, Newman, USA300, MSA817, and Mu3.

The invention also provides DNA sequences encoding the peptides of the invention. Exemplary DNA sequences comprise or consist of a sequence of nucleotides as set forth in SEQ ID NOs: 9, 10, 11, or 12, which encode enolase peptide 214 (SEQ ID NO:1); enolase peptide 215 (SEQ ID NO:2), enolase peptide 213 (SEQ ID NO:5) and enolase peptide 216 (SEQ ID NO:6), respectively, and expression vectors comprising said DNA sequences, or alternative DNA sequences encoding SEQ ID NO's 1, 2, 5 or 6. The present invention also provides a host cell comprising an expression vector comprising a DNA sequence of the invention; e.g. SEQ ID NO: 9, 10, 11, or 12. The host cell may be any suitable prokaryotic or eukaryotic cell. In one embodiment, the host cells are prokaryotic cells such as *E. coli*. The present invention also provides method of producing enolase peptides comprising culturing the host cell and collecting the desired peptides from the host cell or the culture broth.

The invention also provides antibodies against the enolase protein. Such antibodies can be prepared (i.e., raised against the antigen) by suitable methods known to a skilled person.

Among the uses for enolase peptides is the use as a vaccine for the prevention of *staphylococcal* infections and as a target for generating a monoclonal antibody for the prevention or treatment of *staphylococcal* infections. Embodiments of the invention also include one or more of the peptides, nucleotide sequences encoding said peptides, or compositions comprising the peptides or nucleotide sequences thereof, described herein, or a vaccine comprising one or more peptide antigens of the invention (i) for use in, (ii) for use as a medicament for, or (iii) for use in the preparation of a medicament for: (a) therapy (e.g., of the human body); (b) medicine; (c) inhibition of *S. aureus* replication; (d) treatment or prophylaxis of infection by *S. aureus*; or, (e) treatment, prophylaxis of, or delay in the onset or progression of *S. aureus*-associated disease(s), including, but not limited to: skin infections, wound infections, bacteremia, endocarditis, pneumonia, osteomyelitis, toxic shock syndrome, infective endocarditis, folliculitis, furuncle, carbuncle, impetigo, bullous impetigo, cellulitis, botryomyosis, scalded skin syndrome, central nervous system infections, infective and inflammatory eye disease, osteomyelitis and other infections of joints and bones, and respiratory tract infections. The polypeptide immunogens of the invention are also useful for treatment, prophylaxis of, or delay in the onset or progression of *S. aureus*-associated disease common to animals including: bovine mastitis, respiratory disease in swine, skeletal problems, and skin infections in companion animals such as horses, dogs and cats. In these uses, the polypeptide immunogens, compositions thereof, and/or vaccines comprising or consisting of said immunogens or compositions can optionally be employed in combination with one or more anti-bacterial agents (e.g., anti-bacterial compounds; combination vaccines, described infra).

As used herein, the phrase "consists essentially of" when used in connection with the enolase peptides indicates that the referred to amino acids (from the SEQ ID NO) are present and additional amino acids may be present. The additional amino acids can be at the carboxyl terminus, the amino terminus or a combination of the two. In different embodiments 1, 2, 3, 4, 5, 6, 7, 8, 9, 10, 11, 12, 13, 14, 15, 16, 17, 18, 19, or 20 additional amino acids are present. A preferred additional amino acid is an amino-terminal methionine.

As used herein, the term "derivative" refers to a peptide having one or more alterations, which can be an additional amino acid or a chemical modification. In different embodiments, the SEQ ID NO: 1, 2, 5 or 6-related peptide differs from SEQ ID NO: 1, 2, 3, 4, 5 or 6 amino acid alterations or modifications. The term "derivative" also encompasses chemical modifications of the protein (e.g., the modification of functional groups, linking of functional groups (such as alkylation, hydroxylation, phosphorylation, thiolation, carboxylation and the like), linkage to at least one further functional protein domain (such as marker proteins, carrier proteins, proteins holding adjuvant properties and the like; the linkage being directly or via a linker molecule) and to other biologically active molecules (toxins, antibiotics, lipids, carbohydrates, nucleic acids and the like)). In some embodiments, a derivative may have up to 50, 100, 200 or more additional amino acids. For example, the Enolase peptide may be linked to the amino or carboxyl terminus of an antigenic or carrier protein or inserted into an antigenic or carrier protein.

As used herein, the phrase "elicit(s) an immune response" refers to the ability of a enolase peptide, or fragment, variant or derivative thereof, to produce an immune response in a mammal to which it is administered, wherein the response includes the production of elements, such as antibodies, which specifically bind *S. aureus* and/or said peptide, fragment, variant or derivative, and/or which provide a protective effect against *S. aureus* infection.

As used herein, the term "fragment" refers to a continuous segment of the enolase peptide having at least 10 amino acid residues and which is shorter than the full-length enolase peptide. The term includes deletion mutants and small peptides, for example, of at least 8 and more preferably at least 10-15 amino acids in length, which comprise antigenic determinants or epitopes. One or more of such fragments may be joined together. Peptides of this type may be obtained through the application of standard recombinant nucleic acid techniques or synthesized using conventional liquid or solid phase synthesis techniques. For example, reference may be made to solution synthesis or solid phase synthesis as described, for example, in Chapter 9 entitled "Peptide Synthesis" by Atherton and Shephard which is included in a publication entitled "Synthetic Vaccines" edited by Nicholson and published by Blackwell Scientific Publications. Alternatively, peptides can be produced by digestion of a peptide of the invention with proteinases such as endoLys-C, endoArg-C, endoGlu-C and staphylococcins V8-protease. The digested fragments can be purified by, for example, high performance liquid chromatographic (HPLC) techniques.

As used herein, the term "immunologically effective amount" means a sufficient amount of a composition that results in an immune response against *S. aureus* when introduced into a patient. One skilled in the art recognizes that this level may vary. The amount should be sufficient to significantly prevent and/or reduce the likelihood or severity of a *S. aureus* infection.

As used herein, the term "isolated" indicates a different form than found in nature. The different form can be, for example, a different purity than found in nature. In one embodiment, the term refers to material that is substantially or essentially free from components that normally accompany it in its native state.

As used herein, the term "operably linked" means that the transcriptional and translational regulatory nucleic acid is positioned relative to the nucleotide sequence encoding the said peptide, fragment, variant or derivative in such a manner that such transcription is initiatable. The transcriptional and translational regulatory nucleic acid will generally be appropriate for the host cell used for expression. Numerous types of appropriate expression vectors and suitable regulatory sequences are known in the art for a variety of host cells.

As used herein, the term "protective" immunity or immune response, when used in the context of a peptide, immunogen and/or treatment method described herein, indicates a detectable level of protection against *S. aureus* infection. This includes therapeutic and/or prophylactic measures reducing the likelihood of *S. aureus* infection or of obtaining a disorder(s) resulting from such infection, as well as reducing the severity of the infection and/or a disorder(s) resulting from such infection. As such, a protective immune response includes, for example, the ability to reduce bacterial load, ameliorate one or more disorders or symptoms associated with said bacterial infection, and/or delaying the onset of disease progression resulting from *S. aureus* infection.

The level of protection can be assessed using animal models such as those known to those skilled in the art. For example, certain peptides described herein provide protection in both a murine, lethal-challenge model (see, e.g., Thakker et al., *Inf. Immun.* 66: 5183-5189 (1998); Fattom et al., *Inf. Immun.* 64: 1659-1665 (1996)) and a rat, indwelling-catheter, sub-lethal challenge model (see, e.g., Ulphani et al., *Lab Animal Sc.* 49:283-287 (1999); Baddour et al., *J Inf. Dis.* 165:749-53 (1992); Ebert et al., *Human Vaccines* 7(6): 1-9 (2011)).

As used herein, the term "protein," "polypeptide" or "peptide," used interchangeably herein, indicates a contiguous amino acid sequence and does not provide a minimum or maximum size limitation. One or more amino acids present in the protein may contain a post-translational modification, such as glycosylation or disulfide bond formation.

As used herein, the terms "purified" with regard to, for example, a peptide immunogen indicates the presence of such peptide in an environment lacking one or more other peptides with which it is naturally associated and/or is represented by at least about 10% of the total protein present. In different embodiments, the purified peptide represents at least about 50%, at least about 75%, or at least about 95% of the total protein in a sample or preparation.

As used herein, "recombinant peptide" is meant a peptide made using recombinant techniques, i.e., through the expression of a recombinant nucleic acid.

As used herein, the term "recombinant nucleic acid" refers to nucleic acid formed in vitro by the manipulation of nucleic acid into a form not normally found in nature. In this regard, the recombinant nucleic acid preferably comprises an expression vector that may be either a self-replicating extra-chromosomal vector such as a plasmid, or a vector that integrates into a host genome. Generally, such expression vectors include transcriptional and translational regulatory nucleic acid operably linked to the said nucleotide sequence.

As used herein, the term "substantially purified" with regard to, for example, a peptide immunogen indicates the presence of such peptide in an environment lacking all, or most, other peptides with which the peptide is naturally associated. For example, a substantially purified *S. aureus* peptide is present in an environment lacking all, or most, other *S. aureus* peptides. An environment can be, for example, a sample or preparation.

As used herein, the term "variant" refers to peptides in which one or more amino acids have been replaced by different amino acids. It is well understood in the art that some amino acids may be changed to others with broadly similar properties without changing the nature of the activity of the peptide (conservative substitutions). The term "variant" also includes naturally occurring allelic variants.

Peptide Sequences

*S. aureus* enolase is a conserved protein present in all *Staphylococci* and in humans. *Staphylococcal* and human enolase proteins were compared to identify regions that are conserved in *Staphylococci* and differ from sequences in human enolase. Peptides having or consisting of an amino acid sequence as set forth in SEQ ID NO: 1, 2, 5, and 6 are examples of such sequences, which are encompassed by the invention.

SEQ ID NO: 1 corresponds to a peptide consisting of amino acids 213 to 230 of the Enolase protein obtained from *S. aureus* COL strain. The native peptide sequence is as follows:

```
1           KFEGTEDAVE TIIQAIEA
```

In certain embodiments of the invention, there is an amino-terminal methionine to facilitate translation.

SEQ ID NO: 2 corresponds to a peptide consisting of amino acids 419 to 434 peptide of the Enolase obtained from *S. aureus* COL strain. The native peptide sequence is as follows:

```
1           ETAKYDGIKS FYNLDK
```

In certain embodiments of the invention, there is an amino-terminal methionine to facilitate translation.

SEQ ID NO: 3 corresponds to the enolase peptide of SEQ ID NO:1 having an amino terminal His-tag and three additional amino acids at the carboxy terminus (all additional amino acids are underlined). The amino acid sequence is as follows:

```
1      MGHHHHHHHH HHKFEGTEDA VETIIQAIEA AEQ
```

SEQ ID NO: 4 corresponds to this enolase peptide of SEQ ID NO:2 having an amino terminal His-tag and three additional amino acids at the carboxy terminus (all additional amino acids are underlined). The amino acid sequence is as follows:

```
1      MGHHHHHHHH HHETAKYDGI KSFYNLDKAE Q
```

SEQ ID NO 5 is another peptide of the invention and can be used in the same manner as the peptides of SEQ ID NOs 1 and 2. SEQ ID NO: 5 corresponds to a peptide consisting of amino acids 325 to 337 peptide of the Enolase protein obtained from *S. aureus* COL strain. The native peptide sequence is as follows:

```
1           TEILAKGIEN GIG
```

SEQ ID NO 6 is another peptide of the invention and can be used in the same manner as the peptides of SEQ ID NOs 1 and 2. SEQ ID NO: 6 corresponds to a peptide consisting of amino acids 252 to 284 peptide of the Enolase protein obtained from *S. aureus* COL strain. The native peptide sequence is as follows:

```
  1    ENGVYDYSKF EGEHGAKRTA AEQVDYLEQL VDK
```

Preferably, the peptide, or a fragment, variant or derivative thereof, is purified or isolated. In an embodiment, the peptide is substantially purified. Reference to "purified" or "substantially purified" does not require a peptide to undergo any purification and may include, for example, a chemically synthesized peptide that has not been purified.

The use of the terms "fragments", "variants" and "derivatives" is not mutually exclusive. In other words, a fragment can have additions and/or substitutions, a variant can have deletions and/or additions, and a derivative can have deletions and/or substitutions.

Derivatives

In an embodiment of the present invention, a derivative of enolase peptides contain one or more additional regions or moieties covalently joined to the peptide, wherein each region or moiety is independently selected from a region or moiety having at least one of the following properties: facilitates peptide production, facilitates purification, or facilitates peptide stability or enhances the immune response. Such additional regions or moieties can be covalently joined to the peptide through the carboxyl terminus, amino terminus or an internal region of the peptide. The peptide may itself be immunogenic or it may be a non-immunogenic carrier protein. Derivatives include additions to peptides according to SEQ ID NOS: 1, 2, 5 or 6, or variants thereof, wherein said derivatives retain activity eliciting an immune response. "Additions" of amino acids may include fusion of the peptides or variants thereof with other peptides or proteins. In different embodiments, 1, 2, 3, 4, 5, 6, 7, 8, 9, 10, 11, 12, 13, 14, 15, 16, 17, 18, 19, or 20 amino acids are added. In other embodiments at least 1, 2, 3, 4, 5, 6, 7, 8, 9, 10, 11, 12, 13, 14, 15, 16, 17, 18, 19, or 20 amino acids are added. In some embodiments, an upper limit of 30, 35, 40, 45, 50, 55, 60, 65, 70, 75, 80, 85, 90, 95 or 100 amino acids is added. In some embodiments, the peptide may be linked to or inserted into a protein of more than 100 amino acids.

For example, peptide production can be facilitated through the use of an initiation codon (e.g., coding for methionine) suitable for recombinant expression. The methionine may be later removed during cellular processing.

For example, peptide purification can be facilitated by adding a group to the carboxyl or amino terminus to facilitate purification. Examples of groups that can be used to facilitate purification include peptides providing affinity tags. Examples of affinity tags include a six-histidine-tag, trpE, glutathione and maltose-binding protein.

For example, peptide stability can be enhanced by using groups such as polyethylene glycol that may be present on the amino or carboxyl terminus.

An immune response can be enhanced by making the derivative more effective against *S. aureus* or by producing an immune response against another pathogen. Fusion proteins can be added which produce an immunomodulatory response. Particular examples of such proteins include Protein A or glutathione S-transferase (GST). In some embodiments the peptides are conjugated to a immunogenic carrier protein. Derivatives of this kind are useful in presenting the peptides to the immune system of an animal and make useful vaccines. Examples of carrier proteins and conjugations methods are discussed below.

The ability of a peptide to produce an immune response can be improved using groups that generally enhance an immune response. Examples of groups that can be joined to a peptide to enhance an immune response against the peptide include cytokines such as IL-2 (Buchan et al., 2000, *Molecular Immunology* 37:545-552).

Variants

Variants of Enolase peptides of the invention include peptides having amino acid substitutions. In different embodiments 1, 2, 3, 4, 5, 6, 7, 8, 9 or 10 amino acids are substituted. Substitutions may be desirable, for example, to facilitate cloning by introducing restriction sites through amino acid changes. Once a change is introduced it is a matter of straightforward testing using established immunoassays to determine if the immunogenicity of the Enolase peptide has changed. If the peptide is still immunogenic and elicits antibodies that are protective against *Staphylococcal* infections in the challenge models described below, then such variants represent useful embodiments of the present invention.

Generally, in substituting different amino acids while retaining the immunogenic properties of the peptide it is preferable to exchange amino acids having similar properties. Factors that can be taken into account for an amino acid substitution include amino acid size, charge, polarity, and hydrophobicity. The effect of different amino acid R-groups on amino acid properties are well known in the art. (See, for example, Ausubel, *Current Protocols in Molecular Biology*, John Wiley, 1987-2002, Appendix 1C.)

For example, substituting valine for leucine, arginine for lysine, and asparagine for glutamine are good candidates for not causing a change in peptide functioning.

Exemplary conservative substitutions in the peptide may be made according to the following table:

TABLE 1

| ALIPHATIC | Non-polar | G A P |
|           |           | I L V |
|           | Polar - uncharged | C S T M |
|           |           | N Q |
|           | Polar - charged | D E |
|           |           | K R |
| AROMATIC |           | H F W Y |

Substantial changes in function can be made by selecting substitutions that are less conservative than those shown in Table 1. Other replacements would be non-conservative substitutions and relatively fewer of these may be tolerated. Generally, the substitutions which are likely to produce the greatest changes in a peptide's properties are those in which (a) a hydrophilic residue (e.g., Ser or Thr) is substituted for, or by, a hydrophobic residue (e.g., Ala, Leu, Ile, Phe or Val); (b) a cysteine or proline is substituted for, or by, any other residue; (c) a residue having an electropositive side chain (e.g., Arg, His or Lys) is substituted for, or by, an electronegative residue (e.g., Glu or Asp) or (d) a residue having a bulky side chain (e.g., Phe or Trp) is substituted for, or by, one having a smaller side chain (e.g., Ala, Ser) or no side chain (e.g., Gly).

Nucleic acids encoding peptides according to the invention, e.g., SEQ ID NOs: 1, 2, 5 or 6, can be mutated using either random mutagenesis, for example using transposon mutagenesis, or site-directed mutagenesis. The resultant DNA fragments are then cloned into suitable expression hosts such as *E. coli* using conventional technology and clones that retain the desired activity are detected. Where the clones have been derived using random mutagenesis techniques, positive clones would have to be sequenced in order to detect the mutation.

Efficacy of a peptide to induce a protective immune response can be improved through epitope enhancement. Epitope enhancement can be performed using different techniques such as those involving alteration of anchor residues to improve peptide affinity for MHC molecules and those that increase the affinity of the peptide-MHC complex for a T-cell receptor. See Berzofsky et al., 2001, *Nature Review* 1:209-219.

It may also be desirable to incorporate unnatural amino acids and derivatives to improve the properties on the peptides of the invention. Examples of incorporating unnatural amino acids and derivatives during peptide synthesis include but are not limited to, use of 4-amino butyric acid, 6-aminohexanoic acid, 4-amino-3-hydroxy-5-phenylpentanoic acid, 4-amino-3-hydroxy-6-methylheptanoic acid, t-butylglycine, norleucine, norvaline, phenylglycine, ornithine, sarcosine, 2-thienyl alanine and/or D-isomers of amino acids. Unnatural amino acids include those known to one skilled in the art.

Polypeptide Production

Polypeptides can be produced using standard techniques including those involving chemical synthesis and those involving purification from a cell producing the polypeptide. Techniques for chemical synthesis of polypeptides are well known in the art. See, e.g., Vincent, *Peptide and Protein Drug Delivery*, New York, N.Y., Decker, 1990. Techniques for recombinant gene production, introduction into a cell, and recombinant gene expression are well known in the art. Examples of such techniques are provided in references such as Ausubel, *Current Protocols in Molecular Biology*, John Wiley, 1987-2002; and Sambrook et al., *Molecular Cloning, A Laboratory Manual*, 2$^{nd}$ Edition, Cold Spring Harbor Laboratory Press, 1989; and Coligan et al., *Current Protocols in Protein Science* (John Wiley & Sons, Inc. 1995-1997).

Obtaining polypeptides from a cell is facilitated by using recombinant nucleic acid techniques to produce the polypeptide. Recombinant nucleic acid techniques for producing a polypeptide involve introducing, or producing, a recombinant gene encoding the polypeptide in a cell and expressing the polypeptide.

A recombinant gene contains a nucleic acid that encodes a polypeptide, along with regulatory elements for polypeptide expression. The recombinant gene can be present in a cellular genome or can be part of an expression vector.

The regulatory elements that may be present as part of a recombinant gene include those naturally associated with the polypeptide-encoding sequence, as well as exogenous regulatory elements not naturally associated with the polypeptide-encoding sequence. Typically, the transcriptional and translational regulatory nucleic acid may include, but is not limited to, promoter sequences, leader or signal sequences, ribosomal binding sites, transcriptional start and stop sequences, translational start and stop sequences, and enhancer or activator sequences. Exogenous regulatory elements, such as an exogenous promoter, can be useful for expressing a recombinant gene in a particular host or for increasing the level of expression. Generally, the regulatory elements that are present in a recombinant gene include at a minimum a transcriptional promoter, a ribosome binding site, a transcriptional terminator, and an optionally present operator. A preferred element for processing in eukaryotic cells is a polyadenylation signal.

Constitutive or inducible promoters as known in the art are contemplated by the invention. The promoters may be either naturally occurring promoters, or hybrid promoters that combine elements of more than one promoter.

Expression of a recombinant gene in a cell is facilitated through the use of an expression vector. In addition to a recombinant gene, an expression vector usually contains an origin of replication for autonomous replication in a host cell, a selectable marker, a limited number of useful restriction enzyme sites, and a potential for high copy number. Examples of expression vectors are cloning vectors, modified cloning vectors, specifically designed plasmids and viruses. In a preferred embodiment, the expression vector contains a selectable marker gene to allow the selection of transformed host cells. Selection genes are well known in the art and will vary with the host cell used.

Recombinant polypeptides of the invention may be produced by culturing a host cell transformed with an expression vector containing nucleic acid encoding a polypeptide, fragment, variant or derivative according to the invention. The conditions appropriate for protein expression will vary with the choice of expression vector and the host cell. This is easily ascertained by one skilled in the art through routine experimentation. For example, the polypeptides may be prepared by a procedure including the steps of:

(a) preparing a recombinant nucleic acid containing a nucleotide sequence encoding a polypeptide according to the invention, e.g., SEQ ID NOS: 1, 2, 5 or 6, or fragment thereof, or variant or derivative of said polypeptide, which nucleotide sequence is operably linked to transcriptional and translational regulatory nucleic acid;

(b) transfecting or transforming a suitable host cell with the recombinant nucleic acid;

(c) culturing the host cell to express recombinant polypeptide from said recombinant nucleic acid; and (d) isolating the recombinant polypeptide.

In one embodiment, the nucleotide sequence is SEQ ID NO: 9.

In one embodiment, the nucleotide sequence is SEQ ID NO: 10.

In one embodiment, the nucleotide sequence is SEQ ID NO: 11.

In one embodiment, the nucleotide sequence is SEQ ID NO: 12.

Suitable cells for recombinant nucleic acid expression of SEQ ID NO: 9, 10, 11 or 12-related polypeptides are prokaryotes and eukaryotes. Examples of prokaryotic cells include *E. coli*; members of the *Staphylococcus* genus, such as *S. aureus* and *S. epidermidis*; members of the *Lactobacillus* genus, such as *L. plantarum*; members of the *Lactococcus* genus, such as *L. lactis*; members of the *Bacillus* genus, such as *B. subtilis*; members of the *Corynebacterium* genus such as *C. glutamicum*; and members of the *Pseudomonas* genus such as *P. fluorescens*. Examples of eukaryotic cells include mammalian cells; insect cells; and yeast cells, such as members of the Saccharomyces genus (e.g., *S. cerevisiae*), members of the *Pichia* genus (e.g., *P. pastoris*), members of the *Hansenula* genus (e.g., *H. polymorpha*), members of the *Kluyveromyces* genus (e.g., *K. lactis* or *K. fragilis*) and members of the *Schizosaccharomyces* genus (e.g., *S. pombe*).

Alternatively, the host cell may be an insect cell such as, for example, SF9 cells that may be utilized with a baculovirus expression system.

Due to the degeneracy of the genetic code, a large number of different encoding nucleic acid sequences can be used to code for a particular polypeptide. The degeneracy of the genetic code arises because almost all amino acids are encoded by different combinations of nucleotide triplets or "codons." Naturally occurring amino acids are encoded by codons as follows:

A=Ala=Alanine: codons GCA, GCC, GCG, GCU
C=Cys=Cysteine: codons UGC, UGU
D=Asp=Aspartic acid: codons GAC, GAU
E=Glu=Glutamic acid: codons GAA, GAG
F=Phe=Phenylalanine: codons UUC, UUU
G=Gly=Glycine: codons GGA, GGC, GGG, GGU
H=His=Histidine: codons CAC, CAU
I=Ile=Isoleucine: codons AUA, AUC, AUU
K=Lys=Lysine: codons AAA, AAG
L=Leu=Leucine: codons UUA, UUG, CUA, CUC, CUG, CUU
M=Met=Methionine: codon AUG
N=Asn=Asparagine: codons AAC, AAU
P=Pro=Proline: codons CCA, CCC, CCG, CCU
Q=Gln=Glutamine: codons CAA, CAG
R=Arg=Arginine: codons AGA, AGG, CGA, CGC, CGG, CGU
S=Ser=Serine: codons AGC, AGU, UCA, UCC, UCG, UCU
T=Thr=Threonine: codons ACA, ACC, ACG, ACU
V=Val=Valine: codons GUA, GUC, GUG, GUU
W=Trp=Tryptophan: codon UGG
Y=Tyr=Tyrosine: codons UAC, UAU If desired, expression in a particular host can be enhanced through codon optimization. Codon optimization includes use of more preferred codons. Techniques for codon optimization in different hosts are well known in the art.

SEQ ID NO: 1, 2, 5 or 6-related polypeptides may contain post translational modifications, for example, N-linked glycosylation, O-linked glycosylation, or acetylation. Reference to "polypeptide" or an "amino acid" sequence of a polypeptide includes polypeptides containing one or more amino acids having a structure of a post-translational modification from a host cell, such as a yeast host.

Post translational modifications can be produced chemically or by making use of suitable hosts. For example, in *S. cerevisiae* the nature of the penultimate amino acid appears to determine whether the N-terminal methionine is removed. Furthermore, the nature of the penultimate amino acid also determines whether the N-terminal amino acid is $N^\alpha$-acetylated (Huang et al., 1987, *Biochemistry* 26: 8242-8246). Another example includes a polypeptide targeted for secretion due to the presence of a secretory leader (e.g., signal peptide), where the protein is modified by N-linked or O-linked glycosylation (Kukuruzinska et al., 1987, *Ann. Rev. Biochem.* 56:915-944). The expression vector may also include a fusion partner (typically provided by the expression vector) so that the recombinant polypeptide of the invention is expressed as a fusion polypeptide with said fusion partner. The main advantage of fusion partners is that they assist identification and/or purification of said fusion polypeptide.

In order to express said fusion polypeptide, it is necessary to ligate a nucleotide sequence according to the invention into the expression vector so that the translational reading frames of the fusion partner and the nucleotide sequence of the invention coincide.

Well known examples of fusion partners include, but are not limited to, glutathione-S-transferase (GST), Fc portion of human IgG, maltose binding protein (MBP) and hexa-histidine ($HIS_6$), which are particularly useful for isolation of the fusion polypeptide by affinity chromatography. For the purposes of fusion polypeptide purification by affinity chromatography, relevant matrices for affinity chromatography are glutathione-, amylose-, and nickel- or cobalt-conjugated resins respectively. Many such matrices are available in "kit" form, such as the QIAexpress™ system (Qiagen) useful with ($HIS_6$) fusion partners and the Pharmacia GST purification system.

Another fusion partner well known in the art is green fluorescent protein (GFP). This fusion partner serves as a fluorescent "tag" which allows the fusion polypeptide of the invention to be identified by fluorescence microscopy or by flow cytometry. The GFP tag is useful when assessing subcellular localization of the fusion polypeptide of the invention, or for isolating cells which express the fusion polypeptide of the invention.

Preferably, the fusion partners also have protease cleavage sites, such as for Factor $X_a$ or Thrombin, which allow the relevant protease to partially digest the fusion polypeptide of the invention and thereby liberate the recombinant polypeptide of the invention. The liberated polypeptide can then be isolated from the fusion partner by subsequent chromatographic separation.

Fusion partners according to the invention also include within their scope "epitope tags", which are usually short peptide sequences for which a specific antibody is available. Well known examples of epitope tags for which specific monoclonal antibodies are readily available include c-myc, influenza virus haemagglutinin and FLAG tags.

Chemical Modifications

Peptide and polypeptide stability can be enhanced by modifying the carboxyl or amino terminus Examples of possible modifications include amino terminus protecting groups such as acetyl, propyl, succinyl, benzyl, benzyloxycarbonyl or t-butyloxycarbonyl; and carboxyl terminus protecting groups such as amide, methylamide, and ethylamide.

Side chain modifications contemplated by the present invention include modifications of amino groups such as by acylation with acetic anhydride; acylation of amino groups with succinic anhydride and tetrahydrophthalic anhydride; amidination with methylacetimidate; carbamoylation of amino groups with cyanate; pyridoxylation of lysine with pyridoxal-5-phosphate followed by reduction with $NaBH_4$; reductive alkylation by reaction with an aldehyde followed by reduction with $NaBH_4$; and trinitrobenzylation of amino groups with 2,4,6-trinitrobenzene sulphonic acid (TNBS).

The carboxyl group may be modified by carbodiimide activation via O-acylisourea formation followed by subsequent derivitization, by way of example, to a corresponding amide.

The guanidine group of arginine residues may be modified by formation of heterocyclic condensation products with reagents such as 2,3-butanedione, phenylglyoxal and glyoxal.

Sulphydryl groups may be modified by methods such as performic acid oxidation to cysteic acid; formation of mercurial derivatives using 4-chloromercuriphenylsulphonic acid, 4-chloromercuribenzoate; 2-chloromercuri-4-nitrophenol, phenylmercury chloride, and other mercurials; formation of a mixed disulphides with other thiol compounds; reaction with maleimide, maleic anhydride or other substituted maleimide; carboxymethylation with iodoacetic acid or iodoacetamide; and carbamoylation with cyanate at alkaline pH.

Tryptophan residues may be modified, for example, by alkylation of the indole ring with 2-hydroxy-5-nitrobenzyl bromide or sulphonyl halides or by oxidation with N-bromosuccinimide.

Tyrosine residues may be modified by nitration with tetranitromethane to form a 3-nitrotyrosine derivative.

The imidazole ring of a histidine residue may be modified by N-carbethoxylation with diethylpyrocarbonate or by alkylation with iodoacetic acid derivatives.

The invention also contemplates covalently modifying a peptide, fragment or variant of the invention with dinitrophenol, in order to render it more immunogenic in humans.

Peptide Synthesis

Peptides can be produced using techniques well known in the art. Such techniques include chemical and biochemical synthesis. Examples of techniques for chemical synthesis of peptides are provided in Vincent, in *Peptide and Protein Drug Delivery*, New York, N.Y., Dekker, 1990. Examples of techniques for biochemical synthesis involving the introduction of a nucleic acid into a cell and expression of nucleic acids are provided in Ausubel, *Current Protocols in Molecular Biology*, John Wiley, 1987-1998, and Sambrook, et al., in *Molecular Cloning, A Laboratory Manual*, 2nd Edition, Cold Spring Harbor Laboratory Press, 1989.

Carrier Proteins

A carrier protein, as referred to herein, means an immunogenic protein to which the peptides are conjugated. Various carrier proteins are known in the art and have been used in polysaccharide-protein conjugate vaccines. These and other immunogenic proteins can also be used in vaccines of this invention. Preferred carrier proteins are the outer membrane protein complex of Neiserria meningitidis (OMPC), tetanus toxoid protein, CRM, Hepatitis B virus proteins including the Surface antigen protein (HBsAg) and the Core Antigen protein (HB Core), keyhole limpet hemocyanin (KLH), rotavirus capsid proteins and the L1 protein of a bovine Pappiloma virus VLP or human Papilloma Virus VLP, for example, VLPs of HPV type 6, 11 or 16, etc.

For ease of manufacture, one can use a single type of carrier protein to make a conjugate. However, one can also prepare more than one conjugate using a different carrier protein in each one. Then, one can mix the conjugates when formulating the vaccine. In this manner one can provide a vaccine which, in addition to generating an immune response against influenza, also produces an immune response against the different carrier proteins used in the conjugates. Further permutations of conjugates combining various peptides and carrier proteins are also possible, if desired.

A preferred carrier protein is OMPC. OMPC contains numerous reactive sites available for conjugation. The availability of a reactive site for conjugation is determined by the grouping of atoms present and the position of the group in OMPC. Nucleophilic functionalities available for conjugation can be determined using techniques well know in the art. (See Emini et al. U.S. Pat. No. 5,606,030.) One type of group that can be used as a reactive site for conjugation is primary amino groups present on amino acids such as the epsilon amino group of lysine and the alpha amino group of N-terminal amino acids of proteins. In addition, conversion of these amino groups to give the thiolated form of OMPC provides a reactive functionality which may be used for conjugation to thiol reactive peptides. Examples of thiol reactive peptides are bromoacetylated or maleimide derivatized peptides. OMPC can be obtained using techniques well known in the art such as those described by Fu, U.S. Pat. No. 5,494,808.

Another preferred category of carrier proteins is represented by virus capsid proteins that have the capability to self-assemble into virus-like particles (VLPs). Examples of VLPs used as peptide carriers are hepatitis B virus surface antigen(HBsAg) and core antigen (HBcAg) (Pumpens et al., "Evaluation of HBs, HBc, and frCP virus-like particles for expression of human papillomavirus 16 E7 oncoprotein epitopes", *Intervirology*, 45: 24-32 (2002)), hepatitis E virus particles (Niikura et al., "Chimeric recombinant hepatitis E virus-like particles as an oral vaccine vehicle presenting foreign epitopes", *Virology*, 293: 273-280 (2002)), polyoma virus (Gedvilaite et al., "Formation of immunogenic virus-like particles by inserting epitopes into surface-exposed regions of hamster polyomavirus major capsid protein", *Virology*, 273: 21-35 (2000)), and bovine papilloma virus (Chackerian et al., "Conjugation of self-antigen to papillomavirus-like particles allows for efficient induction of protective autoantibodies," *J. Clin. Invest.* 108 (3): 415-423 (2001)). More recently, antigen-presenting artificial VLPs were constructed to mimic the molecular weight and size of real virus particles (Karpenko et al., "Construction of artificial virus-like particles exposing HIV epitopes and the study of their immunogenic properties", *Vaccine*, 21: 386-392 (2003)).

A suspected advantage of using papillomavirus VLPs as peptide antigen carrier is that it allows the presentation of antigenic sequence in an ordered array that is thought to ensure an optimal response from the immune system. In one report, exposure of the antigenic sequence in a matrix that mimics an icosahedral virion was found to abrogate the ability of the humoral immune system to distinguish between self and foreign (Chackerian et al., "Induction of autoantibodies to mouse CCR5 with recombinant papillomavirus particles," *Proc. Natl. Acad. Sci. USA*, 96: 2373-2378 (1999)). By linking mouse self-peptide TNF-α to papilloma virus VLPs high-titers, long-lasting autoantibodies were induced in mice. One of the challenges in using VLPs as minimal antigen carriers is to avoid the decrease in immunogenicity of the developed conjugate vaccine due to the presence of anti-carrier antibodies induced by pre-exposure to the VLP carrier.

The human papillomavirus (HPV) VLPs possess a typical icosahedral lattice structure about 60 nm in size and each is formed by the assembly of 72 L1 protein pentamers (called capsomeres) (Kirnbauer et al., "Papillomavirus L1 major capsid protein self-assembles into virus-like particles that are highly immunogenic", *Proc. Natl. Acad. Sci. USA*, 89: 12180-12184 (1992); Modis et al., "Atomic model of the papilloma virus capsid", *EMBO J.*, 21: 4754-4762 (2002)). Bovine papillomavirus VLPs have been used successfully to carry an antigenic sequence either inserted by genetic fusion into the L1 protein (Chackerian et al., "Induction of autoantibodies to mouse CCR5 with recombinant papillomavirus particles", *Proc. Natl. Acad. Sci. USA*, 96(5): 2373-8 (1999)), or L2 (Greenstone et al., "Chimeric papillomavirus virus-like particle elicit antitumor immunity against the E7 oncoprotein in an HPV 16 tumor model," *Proc. Natl. Acad. Sci. USA*, 95:1800-1805 (1998)) proteins of the VLPs or fused to streptavidin which then is bound to biotinylated VLPs (Chackerian et al., "Conjugation of a self-antigen to papillomavirus-like particles allows for efficient induction of protective autoantibodies", *J. Clin. Invest.*, 108(3): 415-423 (2001)).

The preparation of human and bovine papilloma virus VLPs is well known in the art as indicated by the references cited above and the following exemplary patents and patent publications: U.S. Pat. No. 6,159,729, U.S. Pat. No. 5,840, 306, U.S. Pat. No. 5,820,870 and WO 01/14416.

Examples below describe the preparation and the immunogenicity of exemplary conjugate vaccines obtained by chemically conjugating peptide fragments of influenza to the human papillomavirus (HPV) virus-like particle (VLP). The resulting conjugate molecules, comprised of approximately 800 to 4,000 copies of the antigenic peptide per VLP, were obtained by reacting a C-terminal cysteine residue on the peptides and maleimide-activated HPV VLPs. These conjugates have an average particle size slightly larger than the VLP carrier alone and show enhanced overall stability against chemical and thermal-induced denaturation. The M2-HPV VLP conjugates lost the binding affinity for some anti-HPV conformational antibodies but are fully recognized by anti-M2 antibodies. An influenza M2 peptide-HPV VLP conjugate vaccine was formulated with aluminum adjuvant. Two doses of 30-ng peptide were found to be highly immunogenic and conferred good protection against lethal challenge of influenza virus in mice. These results indicate that HPV VLP can be used as a carrier for influenza peptides in conjugate vaccines.

Using the human papillomavirus VLP system as an antigen carrier for developing chemically coupled influenza peptide conjugate vaccines provides certain advantages. The chemical coupling avoids the potential problems of peptide insertion into the L1 sequence that can interfere with the proper assembly of the VLPs and is much simpler than the biotinylation and binding procedure. Moreover, the results presented show that chemical coupling allows much higher peptide loads per VLP compared to previously reported procedures. Moreover, in the Examples below, the peptide conjugation process did not induce significant alteration in the morphology of HPV VLPs. Therefore, VLPs, including HPV VLPs and the similar bovine papilloma virus VLPs, can be used to construct vaccines within this invention.

Conjugation

The peptides and the carriers of the present invention can be conjugated using any conjugation method in the art. For example, the conjugation can be achieved using SMCC (Succinimidyl 4-[N-maleimidomethyl]cyclohexane-1-carboxylate), sulfosuccinimidyl 4-(N-maleimidomethyl)cyclohexane-1-carboxylate (sSMCC), N-[ε-maleimidocaproyloxy]sulfosuccinimde ester (sEMCS), N-maleimidobenzoyl-N-hydroxysuccinimide ester (MBS), glutaraldehyde, 1-ethyl-3-(3-dimethylaminopropyl)carbodiimide (EDCI), Bis-diazobenzidine (BDB), or N-acetyl homocysteine thiolactone (NAHT).

In the SMCC method, the conjugation is achieved using succinimidyl 4-(N-maleimidomethyl)cyclohexane-1-carboxylate (SMCC). This method is widely used and highly specific (See, e.g., Hermanson, G. T., Bioconjugate Techniques, Second Ed., Elsevier Publishers, p. 788, 2008). SMCC cross-links the SH-group of a cysteine residue to the amino group of a lysine residue on the carrier protein.

In the conjugation reaction using SMCC, the carrier is first activated by reacting the SMCC reagent with the amine (e.g.: lysine) residues of the carrier. After separation of the activated carrier from the excess reagent and the by-product, the cysteine-containing peptide is added and the link takes place by reaction of the SH-group with the maleimide functionional group of the activated carrier.

The conjugation using SMCC can be highly specific for SH-groups. Thus, a cysteine residue in the peptide is essential for facile conjugation. If a peptide does not have a cysteine residue, a cysteine residue should be added to the peptide, preferably at the N-terminus or C-terminus. If the desired epitope in the peptide contains a cysteine, the conjugation should be achieved with a method not using a SMCC activated carrier. If the peptide contains more than one cysteine residue, the peptide should not be conjugated to the carrier using SMCC unless the excess cysteine residue can be replaced or modified.

The linkage should not interfere with the desired epitope in the peptide. The cysteine is preferably separated from the desired epitope sequence with a distance of at least one amino acid as a spacer.

Another conjugation useful in the present invention is achieved using N-acetyl homocysteine thiolactone (NAHT). For example, thiolactones can be used to introduce a thiol functionality onto OMPC, to allow conjugation with maleimidated or Bromo-acetylated-peptides (Tolman et al., *Int. J. Peptide Protein Res.* 41: 455-66 (1993); Conley et al. *Vaccine* 12, 445-451 (1994)).

In particular embodiments of the invention, conjugation reactions to couple the peptide to the carrier protein involve introducing and/or using intrinsic nucleophilic groups on one reactant and introducing and/or using intrinsic electrophilic groups in the other reactant. A preferred activation scheme would be to introduce a nucleophilic thiol group to the carrier protein (preferably OMPC) and adding electrophilic groups (preferably alkyl halides or maleimide) to the peptide. The resulting conjugate will have thiol ether bonds linking the peptide and carrier. Direct reaction of the peptide electrophilic group (maleimide or alkyl halide) and intrinsic nucleophilic groups (preferably primary amines or thiols) of the carrier protein, leading to secondary amine linkages or thiol ether bonds. However, the expected higher reactivity of the thiol nucleophile over the amine under similar reaction conditions would make scheme I preferable. Alternative schemes involve adding a maleimide group or alkyl halide to the carrier and introducing a terminal cysteine to the peptide and/or using intrinsic peptide thiols again resulting in thiol ether linkages.

Linkage

A sulfur containing amino acid contains a reactive sulfur group. Examples of sulfur containing amino acids include cysteine and non-protein amino acids such as homocysteine. Additionally, the reactive sulfur may exist in a disulfide form prior to activation and reaction with carrier. A terminal cysteine can be preferably added to a peptide sequence and used in coupling reactions to a carrier activated with electrophilic groups such as maleimide or alkyl halides. Introduction of maleimide groups using heterobifunctional cross-linkers containing reactive maleimide and activated esters is common. Attempts to achieve high levels of maleimide activation for multimeric protein can lead to cross-linking reactions in which amine groups can react with both functional groups of the cross-linker. This could result in lower levels of available maleimide groups and hence lower peptide loading. The cross-linking of subunits of a multimeric carrier could also effect the immunogenicity and/or stability of the conjugate. For peptides having multiple cysteines, multiple links with the carrier maleimide or alkylhalide groups can occur with a single peptide. This could possibly reduce the peptide loading level. If the multiple links occur through maleimides on different carrier proteins, the possibility of cross-linking of the carrier protein subunits through the peptide can result. Thiolation of OMPC primary amines with N-acetylcysteine lactone can achieve high levels of thiol groups which under appropriate buffer reaction conditions results in minimal cross-linking (via disulfide bond formation) of the carrier subunits (Marburg et al., *J. Am. Chem. Soc.* 108: 5282-5287 (1986)). Activation of the peptide with a single terminal electrophilic group (maleimide or alkyl halide) can lead to high levels peptide loading with a highly directed peptide to carrier coupling.

Linkers

A covalent linker joining a peptide to a carrier is stable under physiological conditions. Examples of such linkers are nonspecific cross-linking agents, monogeneric spacers and bigeneric spacers. Non-specific cross-linking agents and their use are well known in the art. Examples of such reagents and their use include reaction with glutaraldehyde; reaction with N-ethyl-N'-(3-dimethylaminopropyl) carbodiimide, with or without admixture of a succinylated carrier; periodate oxidation of glycosylated substituents followed by coupling to free amino groups of a protein carrier in the presence of sodium borohydride or sodium cyanoborohydride; periodate oxidation of non-acylated terminal serine and threonine residues can create terminal aldehydes which can then be reacted with amines or hydrazides creating Schiff base or hydrazones which can be reduced with cyanoborohydride to secondary amines; diazotization of aromatic amino groups followed by coupling on tyrosine side chain residues of the protein; reaction with isocyanates; or reaction of mixed anhydrides. See, generally, Briand, et al., *J. Imm. Meth.* 78:59 (1985).

Monogeneric spacers and their use are well known in the art. Monogeneric spacers are bifunctional and require functionalization of only one of the partners of the reaction pair before conjugation takes place. An example of a monogeneric spacer and its use involves coupling an immunogenic HCV peptide to one end of the bifunctional molecule adipic acid dihydrazide in the presence of carbodiimide. A diacylated hydrazine presumably forms with pendant glutamic or aspartic carboxyl groups of the carrier. Conjugation then is performed by a second coupling reaction with carrier protein in the presence of carbodiimide.

Bigeneric spacers and their use are well known in the art. Bigeneric spacers are formed after each partner of the reaction pair is functionalized. Conjugation occurs when each functionalized partner is reacted with its opposite partner to form a stable covalent bond or bonds. (See, for example, Marburg, et al., *J. Am. Chem. Soc.* 108:5282-5287 (1986); and Marburg, et al., U.S. Pat. No. 4,695,624.).

Peptide Coupling Load

An advantage of the present invention is that one can achieve various molar ratios of peptide to carrier protein in the conjugate. This "peptide coupling load" on carrier protein can be varied by altering aspects of the conjugation procedure in a trial and error manner to achieve a conjugate having the desired properties. For example, if a high coupling load is desired such that every reactive site on the carrier protein is conjugated to a peptide, one can assess the reactive sites on the carrier and include a large molar excess of peptide in the coupling reaction. If a low density coupling load is desired, one can include a molar ratio of less than 1 mol peptide per mole of reactive sites on the carrier protein.

The particular conditions one chooses will ultimately be guided by the yields achieved, physical properties of the conjugate, the potency of the resulting conjugate, the patient population and the desired dosage one wishes to administer. If the total protein in the vaccine is not an important consideration, one could formulate doses of conjugates of differing coupling loads and different immunogenicities to deliver the same effective dose. However, if total protein or volume is an important consideration, for example, if the conjugate is meant to be used in a combination vaccine, one may be mindful of the total volume or protein contributed by the conjugate to the final combination vaccine. One could then assess the immunogenicity of several conjugates having differing coupling loads and thereafter choose to use a conjugate with adequate immunogenicity and a level of total protein or volume acceptable to add to the combination vaccine.

Generally, there are two main obstacles for obtaining a high peptide load: (i) solubility of the ensuing conjugate, and (ii) solubility of the peptide. These properties are not independent, and manipulations, which improve the latter, can be detrimental to the former. Hence, it is often difficult to obtain a high peptide load.

Therefore, it can be desirable to modify the sequence of a peptide. One method comprises adjusting the isoelectric point (pI) of a peptide by modifying the peptide, and conjugating the peptide to a carrier. As used herein, "adjusting the pI of a peptide" means changing the pI of the peptide to such a range that both the peptide load and the solubility of the conjugate are increased. Frequently, the pI of the peptide is lowered to the range.

The pI of a peptide can be determined either with experiment such as Isoelectric focusing (IEF), or with calculation using appropriate software. The pI, of the peptides can be modified in various ways which change the overall charge of the peptide. The modification can be any change or changes to the peptide that result in the change in the charges of the peptide. The modification can include the replacement, addition, or deletion of amino acid residues in the peptide. The modification can also include modification of the side chains of the residues or N-terminal amino group or C-terminal carboxylate group of the peptide. The methods of such modifications are within the knowledge of one skilled in the art.

The peptide should be modified outside of the immunogenically active sequence, i.e., the desired epitope, thus ensuring maintenance of the immunological properties. The modification should neither involve nor interfere with the desired epitope in the peptide. Since the modifications should not impact on the immunological properties of the peptide-conjugate, changes are preferably introduced at the N and/or C termini of the peptide.

One should also be mindful that the highest coupling load may not always yield the most immunogenic conjugate. Peptide length and coupling load on any given carrier protein may affect the overall immunogenicity of the conjugate. Therefore, one should assess the immunogenicity of a range of coupling loads of any particular peptide on any particular carrier protein. With that information one can then manufacture and formulate vaccines to provide appropriate dosages of conjugate to stimulate acceptable immunogenic responses in patients.

Generation of Antibodies

A SEQ ID NO: 1, 2, 5 or 6-related polypeptide can be used to generate antibodies and antibody fragments that specifically bind to the peptides, the Enolase protein of *S. aureus* or to *S. aureus* bacteria. Such antibodies and antibody fragments have different uses including use in polypeptide purification, *S. aureus* identification, or in therapeutic or prophylactic treatment against *S. aureus* infection.

Antibodies can be polyclonal or monoclonal. Techniques for producing and using antibodies, including human antibodies, are well known in the art (see, e.g., Ausubel, *Current Protocols in Molecular Biology*, John Wiley, 1987-2002; Harlow et al., *Antibodies, A Laboratory Manual*, Cold Spring Harbor Laboratory, 1988; Kohler et al., *Nature* 256:495-497 (1975); Azzazy et al., *Clinical Biochem.* 35:425-445 (2002); Berger et al., *Am. J. Med. Sci.* 324:14-40 (2002)).

Techniques for generating antigen binding protein such as a single-chain antibody, an antibody, or an antibody fragment are well known in the art. Examples of such techniques include the use of phage display technology, identification and humanization of rodent antibodies, and generation of human antibodies using a XenoMouse or Trans-Chromo mouse (e.g., Azzazy et al., *Clinical Biochemistry* 35: 425-445 (2002), Berger et al., *Am. J. Med. Sci.* 324(1): 14-40 (2002))

Murine antibodies can be humanized, and CDR's, can be grafted on to human antibody frameworks using techniques well known in art. Such techniques are generally described with reference to humanizing murine antibodies by grafting murine variable regions onto a human antibody framework and, if needed making further modifications. See, e.g., O'Brien et al., Humanization of Monoclonal Antibodies by CDR Grafting, p 81-100, From *Methods in Molecular Biology* Vol. 207: Recombinant antibodies for Cancer Therapy: Methods and Protocols (Eds. Welschof and Krauss) Humana Press, Totowa, N.J., 2003.

Antigen binding protein are preferably produced using recombinant nucleic acid techniques or through the use of a hybridoma. Recombinant nucleic acid techniques involve constructing a nucleic acid template for protein synthesis. A hybridoma is an immortalized cell line producing the antigen binding protein.

Recombinant nucleic acid encoding an antigen binding protein can be expressed in a host cell that in effect serves as a factory for the encoded protein. The recombinant nucleic acid can provide a recombinant gene encoding the antigen binding protein that exists autonomously from a host cell genome or as part of the host cell genome.

A recombinant gene contains nucleic acid encoding a protein along with regulatory elements for protein expression. Generally, the regulatory elements that are present in a recombinant gene include a transcriptional promoter, a ribosome binding site, a terminator, and an optionally present operator. A preferred element for processing in eukaryotic cells is a polyadenylation signal. Antibody associated introns may also be present. Examples of expression cassettes for antibody or antibody fragment production are well known in art (e.g., Persic et al., *Gene* 187: 9-18 (1997), Boel et al., *J. Immunol. Methods* 239: 153-166 (2000), Liang et al., *J. Immunol. Methods* 247: 119-130 (2001))

Expression of a recombinant gene in a cell is facilitated using an expression vector. Preferably, an expression vector, in addition to a recombinant gene, also contains an origin of replication for autonomous replication in a host cell, a selectable marker, a limited number of useful restriction enzyme sites, and a potential for high copy number. Examples of expression vectors for antibody and antibody fragment production are well known in art (e.g., Persic et al., *Gene* 187: 9-18 (1997), Boel et al., *J. Immunol.* 239: 153-166 (2000), Liang et al., *J. Immunol. Methods* 247: 119-130 (2001))

If desired, nucleic acid encoding an antibody may be integrated into the host chromosome using techniques well known in the art. (See, Ausubel, *Current Protocols in Molecular Biology*, John Wiley, 1987-1998, Mark et al., U.S. Pat. No. 6,743,622.)

A variety of different cell lines can be used for recombinant antigen binding protein expression, including those from prokaryotic organisms (e.g., *E. coli, Bacilli,* and *Streptomyces*) and from Eukaryotic (e.g., yeast, Baculovirus, and mammalian). (Breitling et al., Recombinant Antibodies, John Wiley & Sons, Inc. and Spektrum Akademischer Verlag, 1999.)

Preferred hosts for recombinant antigen binding protein expression are mammalian cells able to produce antigen binding protein with proper post translational modifications. Post translational modifications include disulfide bond formation and glycosylation. Another type of post translational modification is signal peptide cleavage.

Proper glycosylation can be important for antibody function. See Yoo et al., *J. Immunol. Methods* 261: 1-20 (2002); Li et al., *Nature Biotechnol.* 24: 210-215 (2006). Naturally occurring antibodies contain at least one N-linked carbohydrate attached to a heavy chain (Yoo et al., *J. Immunol. Methods* 261: 1-20 (2002)). Additional N-linked carbohydrates and O-linked carbohydrates may be present and may be important for antibody function. Yoo et al., *J. Immunol. Methods* 261:1-20 (2002).

Different types of host cells can be used to provide for efficient post-translational modifications including mammalian host cells and non-mammalian cells. Examples of mammalian host cells include Chinese hamster ovary (CHO), HeLa, C6, PC12, and myeloma cells (Yoo et al., *J. Immunol. Methods* 261: 1-20 (2002); Persic et al., *Gene* 187: 9-18 (1997)). Non-mammalian cells can be modified to replicate human glycosylation (Li et al., *Nature Biotechno.* 24: 210-215 (2006)). Glycoengineered *Pichia pastoris* is an example of such a modified non-mammalian cell (Li et al., *Nature Biotechnol.* 24: 210-215 (2006)).

In lieu of the polyclonal antisera obtained in the production species, monoclonal antibodies may be produced using the standard method as for example, described in an article by Kohler and Milstein (*Nature* 256: 495-497 (1975)) which is herein incorporated by reference, or by more recent modifications thereof as for example, described in Coligan et al., *Current Protocols in Protein Science* (John Wiley & Sons, Inc. 1995-1997) by immortalizing spleen or other antibody producing cells derived from a production species which has been inoculated with one or more of the polypeptides, fragments, variants or derivatives of the invention.

A hybridoma can be produced using techniques such as those described in Ausubel, *Current Protocols in Molecular Biology*, John Wiley, 1987-1998, Harlow et al., Antibodies, A Laboratory Manual, Cold Spring Harbor Laboratory, 1988, and Kohler et al., *Nature* 256: 495-497 (1975).

The invention also includes within its scope antibodies which comprise Fc or Fab fragments of the polyclonal or monoclonal antibodies referred to above. Alternatively, the antibodies may comprise single chain Fv antibodies (scFvs) against the peptides of the invention. Such scFvs may be prepared, for example, in accordance with the methods described respectively in U.S. Pat. No 5,091,513, European Patent No. 239,400 or as described in Winter et al. (*Nature* 349: 293 (1991)).

Pharmaceutical Compositions

A further feature of the invention is the use of one or more enolase polypeptide, fragment, variant or derivative of the invention ("immunogenic agents"), either alone or in combination with one or more additional antigens, as active ingredients in a composition, preferably an immunogenic composition or vaccine, for treating patients with an *S. aureus* infection, reducing the progression, onset or severity of pathological symptoms associated with *S. aureus* infection and/or reducing the likelihood of an *S. aureus* infection. Suitably, the composition comprises a pharmaceutically acceptable carrier.

In some embodiment of the invention described above, the pharmaceutical compositions are used in human patients. In alternative embodiments, the pharmaceutical compositions are used in non-human patients.

By "pharmaceutically-acceptable carrier" is meant a solid or liquid filler, diluent or encapsulating substance that may be safely used in systemic administration. Depending upon the particular route of administration, a variety of pharmaceutically acceptable carriers, well known in the art may be used. These carriers may be selected from a group including sugars, starches, cellulose and its derivatives, malt, gelatine, talc, calcium sulfate, vegetable oils, synthetic oils, polyols, alginic acid, phosphate buffered solutions including phosphate buffered saline, emulsifiers, isotonic saline, and pyrogen-free water. In particular, pharmaceutically acceptable carriers may contain different components such as a buffer, sterile water for injection, normal saline or phosphate-buffered saline, sucrose, histidine, salts and polysorbate. Terms such as "physiologically acceptable", "diluent" or "excipient" can be used interchangeably.

Compositions of the present invention suitable for oral or parenteral administration may be presented as discrete units such as capsules, sachets or tablets each containing a predetermined amount of one or more therapeutic agents of the invention, as a powder or granules or as a solution or a suspension in an aqueous liquid, a non-aqueous liquid, an oil-in-water emulsion or a water-in-oil liquid emulsion. Such compositions may be prepared by any of the methods of pharmacy but all methods include the step of bringing into association one or more immunogenic agents as described above with the carrier which constitutes one or more necessary ingredients. In general, the compositions are prepared by uniformly and intimately admixing the immunogenic agents of the invention with liquid carriers or finely divided solid carriers or both, and then, if necessary, shaping the product into the desired presentation.

The above compositions may be used as therapeutic or prophylactic vaccines. Accordingly, the invention extends to the production of vaccines containing as actives one or more of the immunogenic agents of the invention. Any suitable procedure is contemplated for producing such vaccines. Exemplary procedures include, for example, those described in New Generation Vaccines (1997, Levine et al., Marcel Dekker, Inc. New York, Basel Hong Kong), which is incorporated herein by reference.

A peptide of the invention can be conjugated with an immunogenic carrier. Useful carriers are well known in the art and include for example: thyroglobulin; albumins such as human serum albumin; toxins, toxoids or any mutant cross-reactive material (CRM) of the toxin from tetanus, diptheria, pertussis, *Pseudomonas, E. coli, Staphylococcus*, and *Streprococcus*; polyamino acids such as poly(lysine:glutamic acid); influenza; Rotavirus VP6, Parvovirus VP1 and VP2; hepatitis B virus core protein; hepatitis B virus recombinant vaccine and the like. Alternatively, a fragment or epitope of a carrier protein or other immnogenic protein may be used. For example, a peptide of the invention can be coupled to a T cell epitope of a bacterial toxin, toxoid or CRM. In this regard, reference may be made to U.S. Pat. No. 5,785,973, which is incorporated herein by reference.

In addition, a polypeptide, fragment, variant or derivative of the invention may act as a carrier protein in vaccine compositions directed against *S. aureus*, or against other bacteria or viruses.

In a further embodiment, the nucleotide sequence may be used as a vaccine in the form of a "naked DNA" vaccine as is known in the art. For example, an expression vector of the invention may be introduced into a mammal, where it causes production of a polypeptide in vivo, against which the host mounts an immune response as for example described in Barry et al. (*Nature* 377:632-635 (1995)).

These dosage forms may also include injecting or implanting controlled releasing devices designed specifically for this purpose or other forms of implants modified to act additionally in this fashion. Controlled release of the therapeutic agent may be affected by coating the same, for example, with hydrophobic polymers including acrylic resins, waxes, higher aliphatic alcohols, polylactic and polyglycolic acids and certain cellulose derivatives such as hydroxypropylmethyl cellulose. In addition, the controlled release may be affected by using other polymer matrices, liposomes and/or microspheres.

Adjuvants

Adjuvants are substances that can assist an immunogen (e.g., a polypeptide, pharmaceutical composition containing a polypeptide) in producing an immune response. Adjuvants can function by different mechanisms such as one or more of the following: increasing the antigen biologic or immunologic half-life; improving antigen delivery to antigen-presenting cells; improving antigen processing and presentation by antigen-presenting cells; and, inducing production of immunomodulatory cytokines (Vogel, *Clinical Infectious Diseases* 30 (suppl. 3):S266-270, 2000). In one embodiment of the present invention, an adjuvant is used.

A variety of different types of adjuvants, which are known to those skilled in the art, can be employed to assist in the production of an immune response. Examples of particular adjuvants include aluminum hydroxide; aluminum phosphate, aluminum hydroxyphosphate sulfate or other salts of aluminum; calcium phosphate; DNA CpG motifs; monophosphoryl lipid A; cholera toxin; *E. coli* heat-labile toxin; pertussis toxin; muramyl dipeptide; Freund's incomplete adjuvant; MF59; SAF; immunostimulatory complexes; liposomes; biodegradable microspheres; saponins; nonionic block copolymers; muramyl peptide analogues; polyphosphazene; synthetic polynucleotides; lymphokines such as IFN-γ; IL-2; IL-12; and ISCOMS. (Vogel, Clin Infect Dis 30 (suppl 3):S266-270, 2000; Klein et al., 2000, J Pharm Sci 89:311-321; Rimmelzwaan et al., 2001, *Vaccine* 19:1180-1187; Kersten, 2003, *Vaccine* 21:915-920; O'Hagen, 2001, *Curr. Drug Target Infect. Disord.* 1:273-286.

Administration

One or more of the SEQ ID NO: 1, 2, 5 or 6-related polypeptides and immunogens described herein can be formulated and administered to a patient using the guidance provided herein along with techniques well known in the art. Guidelines for pharmaceutical administration in general are provided in, for example, Vaccines Eds. Plotkin and Orenstein, W. B. Sanders Company, 1999; *Remington's Pharmaceutical Sciences* 20$^{th}$ Edition, Ed. Gennaro, Mack Publishing, 2000; and Modern Pharmaceutics 2$^{nd}$ *Edition*, Eds. Banker and Rhodes, Marcel Dekker, Inc., 1990.

Accordingly, the invention provides a method for inducing a protective immune response in a patient against an *S. aureus* infection comprising the step of administering to the patient an immunologically effective amount of any of the vaccines or pharmaceutical compositions described herein. In one embodiment of this aspect of the invention, the patient is a human. In alternative embodiments, the patient is a non-human mammal.

Also provided by the invention is a method for treating *S. aureus* infection, or for treating any pathological condition associated with *S. aureus* infection, the method comprising the step of administering to the patient an immunologically effective amount of any of the vaccines or pharmaceutical compositions described herein. In one embodiment of this aspect of the invention, the patient is a human. In alternative embodiments, the patient is a non-human mammal.

Any suitable route of administration may be employed for providing a patient with the composition of the invention. For example, oral, parenteral, intravenous, intra-articular, intra-muscular, intra-dermal, subcutaneous, inhalational, intraperitoneal, transdermal and the like may be employed. Intra-muscular and subcutaneous injection is appropriate, for example, for administration of immunogenic compositions, vaccines and DNA vaccines.

The above compositions may be administered in a manner compatible with the dosage formulation, and in such amount as is immunogenically-effective to protect patients from *S. aureus* infection. The dose administered to a patient, in the context of the present invention, should be sufficient to effect a beneficial response in a patient over time such as a reduction in the level of *S. aureus*, or to inhibit infection by *S. aureus*. The quantity of the immunogenic agent(s) to be administered may depend on the subject to be treated inclusive of the age, sex, weight and general health condition thereof. In this regard, precise amounts of the immunogenic agent(s) required to be administered will depend on the judgment of the practitioner. In determining the effective amount of the immunogenic agent to be administered in the treatment or prophylaxis against *S. aureus*, the physician may evaluate circulating plasma levels, progression of disease, and the production of anti-*S. aureus* antibodies. In any event, suitable dosages of the immunogenic agents of the invention may be readily determined by those of skill in the art. Such dosages may be in the order of nanograms to milligrams of the immunogenic agents of the invention.

Suitable dosing regimens are preferably determined taking into account factors well known in the art including age, weight, sex and medical condition of the patient; the route of administration; the desired effect; and the particular compound employed. The immunogen can be used in multi-dose formats. It is expected that a dose would consist of the range of 1.0 mg to 1.0 mg total polypeptide. In different embodiments of the present invention, the dosage range is from 5.0 mg to 500 mg, 0.01 mg to 1.0 mg, or 0.1 mg to 1.0 mg.

For combination vaccinations, each of the polypeptides can be administered together in one composition or separately in different compositions. A composition comprising one or more enolase peptides, fragments, or derivatives of the invention can be administered concurrently with one or more desired immunogens. The term "concurrently" is not limited to the administration of the therapeutic agents at exactly the same time, but rather it is meant that the enolase polypeptides described herein and the other desired immunogen(s) are administered to a subject in a sequence and within a time interval such that the they can act together to provide an increased benefit than if they were administered otherwise. For example, each therapeutic agent may be administered at the same time or sequentially in any order at different points in time; however, if not administered at the same time, they should be administered sufficiently close in time so as to provide the desired therapeutic effect. Each therapeutic agent can be administered separately, in any appropriate form and by any suitable route.

The timing of doses depends upon factors well known in the art. After the initial administration one or more additional doses may be administered to maintain and/or boost the appropriate immune response. An example of a dosing regime would be day 1, 1 month, a third dose at either 4, 6 or 12 months, and additional booster doses at distant times as needed.

Patients For Inducing Protective Immunity

A "patient" refers to a mammal capable of being infected with *S. aureus*. In one embodiment, a patient is a human. A patient can be treated prophylactically or therapeutically. Prophylactic treatment provides sufficient protective immunity to reduce the likelihood, or severity, of a *S. aureus* infection. Therapeutic treatment can be performed to reduce the severity of a *S. aureus* infection.

Prophylactic treatment can be performed using a pharmaceutical composition containing a polypeptide or immunogen described herein. Pharmaceutical compositions can be administered to the general population, to infants, children, or the elderly, to immunocompromised patients or to those persons at an increased risk of *S. aureus* infection.

Those "in need of treatment" include those already with an infection, as well as those prone to have an infection or in which a reduction in the likelihood of infection is desired. Persons with an increased risk of *S. aureus* infection include health care workers; hospital patients; patients with a weakened immune system; patients undergoing surgery; patients receiving foreign body implants, such as catheter or a vascular device; patients facing therapy leading to a weakened immunity; and, persons in professions having an increased risk of burn or wound injury. See The Staphylococci in Human Disease, Crossley and Archer (ed.), Churchill Livingstone Inc. 1997.

Non-human patients that can be infected with *S. aureus* include cows, pigs, sheep, goats, rabbits, horses, dogs, cats, rats and mice. Treatment of non-human patients is useful in both protecting pets and livestock (e.g. against Staph-related disease common to animals such as bovine mastitis) and evaluating the efficacy of a particular treatment. In addition to the obvious benefits of preventing, or reducing the likelihood or severity of clinical manifestations of *S. aureus* infections in vaccinated animals, additional benefits include the reduction of costs resulting from sick and underproductive livestock animals to a farmer; the reduction in the need for quarantine measures to a human or veterinary clinic by reducing the number of *S. aureus* infected patients, and reduced need for repeated rigorous decontamination of equipment and facilities; and a reduction of the number of *S. aureus* carriers in the human and animal populations, which reduces their potential contamination and spread to others.

Combination Vaccines

An immunogenic agent according to the invention can be mixed, conjugated or fused with other antigens. For example, Enolase peptides can be used alone or in combination with other immunogens to generate a vaccine that is protective against *staphylococcal* disease or other bacterial diseases; depending on the other immunogens use.

SEQ ID NO: 1, 2, 5 or 6-related polypeptides can be used alone, or in combination with other immunogens, to induce an immune response. Additional immunogens that may be present include one or more additional *S. aureus* immunogens, one or more immunogens targeting one or more other *Staphylococcus* organisms such as *S. epidermidis, S. haemolyticus, S. warneri*, or *S. lugunensi*.

A vaccine targeting *S. aureus* can be achieved using suitable *S. aureus* polysaccharides or polypeptides as vaccine components. Examples of polysaccharides that may be employed as possible vaccine components include *S. aureus* type 5 and type 8 capsular polysaccharides. See Shinefield et al., *N. Eng. J. Med.* 346: 491-496 (2002). Examples of polypeptides that may be employed as possible vaccine components include clumping factor, collagen adhesin, and fibrinogen binding proteins. See Mamo et al., *FEMS Immu-* nol. Med. Mic. 10:47-54 (1994); Nilsson et al., 1998, *J. Clin. Invest.* 101:2640-2649; Josefsson et al., *J. Infect. Dis.* 184:1572-1580 (2001).

The immunogenic agents of the invention may be administered as multivalent subunit vaccines in combination with antigens of other infectious organisms inclusive of the pathogenic bacteria *H. influenzae, M. catarrhalis, N gonorrhoeae, E. coli, S. pneumoniae,* etc.

In one embodiment, the additional immunogen is IsdB (also known as ORF0657) or related polypeptides. (see SEQ ID NO:7 herein. Also described in US Publication No. 2006/0177462 which is incorporated by reference herein in its entirety). Reference to an IsdB immunogen refers to an immunogen that produces a protective immune response that recognizes the IsdB protein in *S. aureus.* In different embodiments, the IsdB protein in *S. aureus* recognizes at least one or more of the following strains: COL, Becker, MW2, N315, Newman, USA300, MSA817, and Mu3. The ability of an IsdB immunogen to provided protective immunity is illustrated in, for example, US Publication No. 2006/0177462.

In one embodiment, the polypeptide of the invention is combined with IsdB (also known as ORF0657n) or related polypeptides. See U.S. Patent Application Publication No. 2006/0177462, incorporated by reference herein in its entirety. Reference to an IsdB immunogen refers to an immunogen that produces a protective immune response that recognizes the IsdB protein in *S. aureus.* An example of an IsdB immunogen is the polypeptide having the sequence of SEQ ID NO: 7.

In different embodiments, the IsdB immunogen recognizes at least one or more of the following strains: COL, Becker, MW2, N315, Newman, USA300. The ability of IsdB immunogens to provided protective immunity is illustrated, in for example, U.S. Patent Application Publication No. 2006/0177462, incorporated by reference herein in its entirety.

In additional embodiments, the IsdB immunogen comprises a polypeptide region, said region (a) is at least 90%, at least 94%, at least 95% or at least 99% identical to SEQ ID NO: 7 or a fragment thereof (including, but not limited to, amino acids 42-486, 42-522 and 42-608 of SEQ ID NO: 7); (b) differs from SEQ ID NO: 7 or a fragment thereof (including, but not limited to, amino acids 42-486, 42-522 and 42-608 of SEQ ID NO: 7) by 0, 1, 2, 3, 4, 5, 6, 7, 8, 9, 10, 11, 12, 13, 14, 15, 16, 17, 18, 19, 20, 21, 22, 23, 24, or 25 alterations, or up to 50 alterations; or (c) consists essentially of or consists of SEQ ID NO: 7 or a fragment thereof (including, but not limited to, amino acids 42-486, 42-522 and 42-608 of SEQ ID NO: 7). Examples of alterations include amino acid substitutions, deletions, and insertions.

As stated above, the invention relates to compositions and vaccine comprising combinations of one or more of the enolase peptide immunogens of the invention with Isdb (a.k.a. ORF0657n) or ORF0657n-related polypeptides and a pharmaceutically acceptable carrier (Anderson et al., International Publication no. WO 05/009379). Examples of one or more additional or alternative immunogens that can be included in the compositions and vaccines of the invention described herein include, but are not limited to: ORF0657/ORF0190 hybrid polypeptides (Anderson et al., International Publication no. WO 05/009378); sai-1-related polypeptides (Anderson et al., International Publication no. WO 05/79315); ORF0594-related polypeptides (Anderson et al., International Publication no. WO 05/086663); ORF0826-related polypeptides (Anderson et al., International Publication no. WO 05/115113); PBP4-related polypeptides (Anderson et al., International Publication no. WO 06/033918); AhpC-related polypeptides and AhpC-AhpF compositions (Kelly et al. International Publication No. WO 06/078680); SACOL1902-related polypeptides (WO 10/062814); SACOL0912-related polypeptides (WO 10/062815); SA0024-related polypeptides (WO 07/001361); SACOL 2451-related polypeptides; SACOL2412-related polypeptides (PCT/US 11/43499), SACOL1789-related polypeptides (PCT/US11/43274), *S. aureus* type 5 and type 8 capsular polysaccharides (Shinefield et al., 2002, *N. Eng. J. Med.* 346:491-496); collagen adhesin, fibrinogen binding proteins, and clumping factor (Mamo et al., 199, *FEMS Immunol. Med. Microbiol.* 10:47-54; Nilsson et al., 1998, *J. Clin. Invest.* 101:2640-2649; Josefsson et al., 2001, *J. of Infect. Dis.* 184:1572-1580); and polysaccharide intercellular adhesin and fragments thereof (Joyce et al., 2003, *Carbohydrate Research* 338:903-922).

The amount of IsdB can be from 1 to 500 µg, 5 to 200 µg, 10 to 100 µg. Exemplary dosages include, but are not limited to, 10, 20, 30, 40, 50, 60, 70, 80, 90, or 100 µg.

The specific embodiments described herein are offered by way of example only, and the invention is to be limited only by the terms of the appended claims along with the full scope of equivalents to which such claims are entitled. Indeed various modifications of the invention, in addition to those shown and described herein will become apparent to those skilled in the art from the foregoing description and accompanying drawings. Such modifications are intended to fall within the scope of the appended claims.

The following examples illustrate, but do not limit the invention.

Example 1

Peptide Synthesis and Conjugation

Peptides were synthesized by microwave chemistry on a liberty synthesizer on NovaPEG Rink amide resin at 0.15 mmol scale. Alternatively, peptides were synthesized by microwave chemistry using ChemMatrix amide resin at 0.15 mmol scale.

Conjugation to Biotin.

Peptides were purified and conjugated to biotin to be used to determine antibody ELISA titers in sera generated from immunization of animals with the peptides conjugated to carrier proteins. For example, the peptide of SEQ ID NO:1 gave:

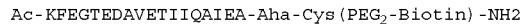

Ac-KFEGTEDAVETIIQAIEA-Aha-Cys(PEG$_2$-Biotin)-NH2

Yield: 3.86 mg. Purity was >95%.

And the peptide of SEQ ID NO: 2 gave:

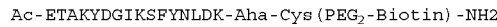

Ac-ETAKYDGIKSFYNLDK-Aha-Cys(PEG$_2$-Biotin)-NH2

Yield: 5.27 mg. Purity was >95%.

Conjugation to Carrier Protein.

Peptides containing terminal cysteine residues for conjugation were purified following solid phase synthesis and reacted with maleimide activated CRM. CRM was maleimide-activated on surface-accessible lysine residues by reacting with a ten fold molar excess (relative to CRM surface lysine content) of SMCC in HEPES buffered saline containing 5 mM EDTA at 20-25° C. for 4 hours. The maleimide activated CRM was purified of un-reacted SMCC using a desalting column. Peptide conjugates were prepared by mixing each peptide with an amount of maleimide activated CRM such that the molar ratio of peptide cysteine residues to CRM maleimide residues was 2:1. This reaction was carried out in HEPES buffered saline containing 5mM EDTA at 2-8° C. for 12-18 hours. Un-reacted maleimide groups were quenched with an excess of 2-mercaptoethanol and the conjugates were separated from free peptide and low molecular weight reactants by extensive dialysis versus HEPES buffered saline. The peptide conjugates were analyzed by gel electrophoresis to provide visual confirmation of conjugation, and by amino acid analysis to determine the peptide loading ratio and total protein concentration. Total protein concentrations were also determined by BCA assay.

TABLE 2

Analytical data from a representative conjugation is shown in the following table:

| | Enolase Peptide No. | | | |
|---|---|---|---|---|
| | 213 | 214 | 215 | 216 |
| | | (SEQ ID NO) | | |
| | SEQ ID NO: 5 | SEQ ID NO: 1 | SEQ ID NO: 2 | SEQ ID NO: 6 |
| BCA Total Protein Concentration (mg/mL) | 1.037 | 0.848 | 1.07 | 1.329 |
| AAA Total Protein Concentration (mg/mL) | 0.602 | 0.677 | 0.6 | 1.294 |
| Peptide Loading Ratio (mole peptide/mole CRM) | 26.6 | 22.3 | 24.8 | 29.8 |
| Peptide Weight Percent | 43% | 47% | 48% | 67% |
| Peptide Concentration (mg/mL) | 0.444 | 0.394 | 0.517 | 0.895 |

Example 2

Formulation

The Enolase peptide CRM197 conjugates were formulated along with the CRM and Sdre controls in Merck Alum, an aluminum hydroxyphosphate sulfate adjuvant, at 0.15 mg/ml, i.e. peptide SEQ ID NO: 1, peptide SEQ ID NO: 2, peptide SEQ ID NO:5, peptide SEQ ID NO:6 and CRM.

Example 3

Murine Lethal Challenge Model

Female Balb/c mice (6-9 wks of age, 20 animals per group) were immunized 3× intramuscularly with 20 ng of CRM (negative control), SdrE (control) or Enolase peptides conjugated to CRM 197 on days 1, 7 and 21. Mice were challenged with a lethal dose ($6.0 \times 10^8$ CFU) of S. aureus Becker (strain provided by Chia Lee, University of Arkansas for Medical Sciences, Little Rock); grown in TSA (tryptone soy agar; Becton Dickinson, San Jose, Calif.) on day 35 and survival was monitored over a 10 day period.

TABLE 3

Survival data for 10 days post challenge with Peptide - CRM Conjugates

| Immunogen | Survival No. | % Survival |
|---|---|---|
| SdrE Control | 08/20 | 40 |
| Enolase #214 (SEQ ID NO: 1) | 09/20 | 45 |
| Enolase #215 (SEQ ID NO: 2) | 06/20 | 30 |
| CRM Control | 02/20 | 10 |

*P value 0.0221

Data obtained shows survival was enhanced in mice immunized with Enolase peptides versus the negative control antigen CRM, which was significant protection p=0.0221. See Table 3.

Mice were bled before immunization and again before lethal challenge. The sera were tested in an ELISA using enolase from S. aureus. The antisera had no reactivity to human enolase (data not shown).

TABLE 4

| Antigen | ELISA titers | **P value |
|---|---|---|
| SEQ ID NO: 1 Post immunization | 62,635 | 0.0533 |
| Pre-immunization | 400 | |
| SEQ ID NO: 2 Post immunization | 97,200 | 0.0477 |
| Pre-immunization | 400 | |

The data presented in Table 4 shows that the Enolase peptide conjugates induce a significant immune response in immunized animals, supporting the increased survival rates seen in Table 3.

In this experiment, none of the Enolase peptides were positive when compared to SdrE, the negative control. However when compared with the internal control antigen CRM, Enolase peptides have 20% or more difference in survival and are significantly different from the negative control antigen CRM.

Example 4

Rat Indwelling Catheter Model

Female Sprague Dawley rats (6-9 wks of age) were immunized 3× intramuscularly with 20 μg of CRM (control), or Enolase peptides conjugated to CRM 192 on days 0, 7 and 21. On day 35 rats were cannulated via the jugular vein. Rats were rested for 10 days post surgery. Rats were challenged with a sub-lethal dose ($2.0 \times 10^9$ CFU) of S. aureus Becker (Strain provided by Chia Lee, University of Arkansas for Medical Sciences, Little Rock); grown in TSA (tryptone soy agar; Becton Dickinson, San Jose, Calif.) on day 45. The catheters were removed at 24 hours post challenge and evaluated for colony forming units of S. aureus on the catheter. Data shown in FIG. 2 indicates that the enolase conjugates 214 (SEQ ID NO:1) and 216 (SEQ ID NO:6) had activity in this model, whereas conjugates 213 (SEQ ID NO:5) and 215 (SEQ ID NO:2) did not. This corresponds to the increased titers for these two conjugates, as shown in Table 5, against S. aureus enolase. Antisera from the rats did not cross react with human enolase.

TABLE 5

| | ELISA titers (end point) day 28 (1 week post dose 3) geo mean of n = 5 | |
|---|---|---|
| Enolase peptide | Anti-*S. aureus* enolase | Anti-human enolase |
| 213 (SEQ ID NO: 5) | 692 | 400 |
| 214 (SEQ ID NO: 1) | 97,200 | 400 |
| 215 (SEQ ID NO: 2) | 692 | 400 |
| 216 (SEQ ID NO: 6) | 221,568 | 400 |
| CRM | 526 (anti-CRM) | 400 |

What is claimed is:

1. An isolated enolase peptide derivative, wherein said derivative comprises an enolase peptide and one or more additional not naturally associated regions or moieties covalently joined to said amino acid sequence, wherein the enolase peptide consists of a sequence of amino acids as set forth in SEQ ID NO:6 or consists essentially of SEQ ID NO:6 and between 1 and 10 additional amino acids, wherein each region or moiety is independently selected from a region or moiety having at least one of the following properties: enhances the immune response, facilitates purification, or facilitates polypeptide stability.

2. An immunogenic composition able to induce a protective immune response in a patient against S. aureus infection comprising an immunologically effective amount of an isolated enolase peptide, and a pharmaceutically acceptable carrier, and an amount of adjuvant that enhances the immune response, wherein the enolase peptide consists of SEQ ID NO:6 or is a derivative of SEQ ID NO:6 consisting essentially of SEQ ID NO:6 and between 1 and 10 additional amino acids.

3. The immunogenic composition of claim 2, wherein the enolase peptide is a derivative of SEQ ID NO:6 consisting of the amino acid sequence as set forth in SEQ ID NO: 6 with an additional N-terminal methionine.

* * * * *